United States Patent
Rister et al.

(10) Patent No.: US 9,456,810 B2
(45) Date of Patent: Oct. 4, 2016

(54) SURGICAL INSTRUMENT HANDLE ASSEMBLY

(71) Applicant: Smith & Nephew, Inc., Memphis, TN (US)

(72) Inventors: David Wayne Rister, Nesbit, MS (US); Brian David Davis, Millington, TN (US)

(73) Assignee: Smith & Nephew, Inc., Memphis, TN (US)

( * ) Notice: Subject to any disclaimer, the term of this patent is extended or adjusted under 35 U.S.C. 154(b) by 818 days.

(21) Appl. No.: 13/741,175

(22) Filed: Jan. 14, 2013

(65) Prior Publication Data

US 2013/0197489 A1    Aug. 1, 2013

Related U.S. Application Data

(60) Provisional application No. 61/586,494, filed on Jan. 13, 2012.

(51) Int. Cl.
*A61B 17/00* (2006.01)
*A61B 17/16* (2006.01)

(52) U.S. Cl.
CPC .......... *A61B 17/00* (2013.01); *A61B 17/1659* (2013.01); *A61B 17/1668* (2013.01); *A61B 2017/0042* (2013.01); *A61B 2017/0046* (2013.01)

(58) Field of Classification Search
CPC .............. A61B 2017/0046; A61B 2017/0042; A61B 17/1668; B23D 51/14
See application file for complete search history.

(56) References Cited

U.S. PATENT DOCUMENTS

| | | | |
|---|---|---|---|
| 5,443,471 A * | 8/1995 | Swajger | 606/99 |
| 7,591,821 B2 | 9/2009 | Kelman | |
| 7,935,125 B2 | 5/2011 | Bastian et al. | |
| 2007/0233134 A1* | 10/2007 | Bastian et al. | 606/85 |
| 2009/0275948 A1 | 11/2009 | Kelman | |
| 2010/0121331 A1 | 5/2010 | Sharp et al. | |
| 2011/0247633 A1 | 10/2011 | Kelman | |
| 2011/0295259 A1 | 12/2011 | Kelman | |

* cited by examiner

*Primary Examiner* — Gary Jackson
*Assistant Examiner* — Scott T Luan
(74) *Attorney, Agent, or Firm* — Taft Stettinius & Hollister LLP

(57) ABSTRACT

A surgical instrument handle assembly configured for rigid and releasable connection to orthopedic devices including orthopedic shaping or cutting members such as a broaches, reamers and/or osteotomes adapted to prepare the intramedullary canal of a femur in total hip arthroplasty procedures.

36 Claims, 17 Drawing Sheets

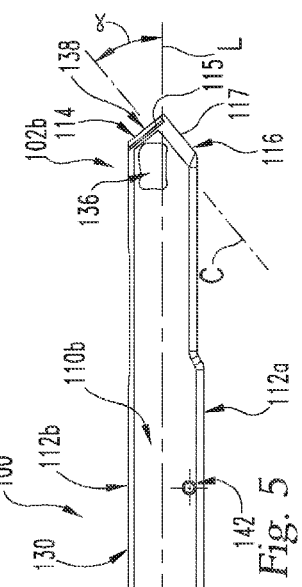
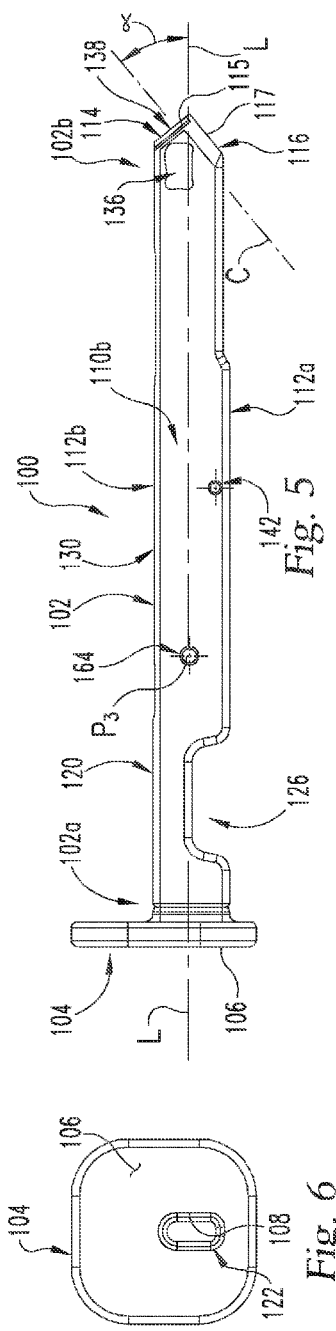
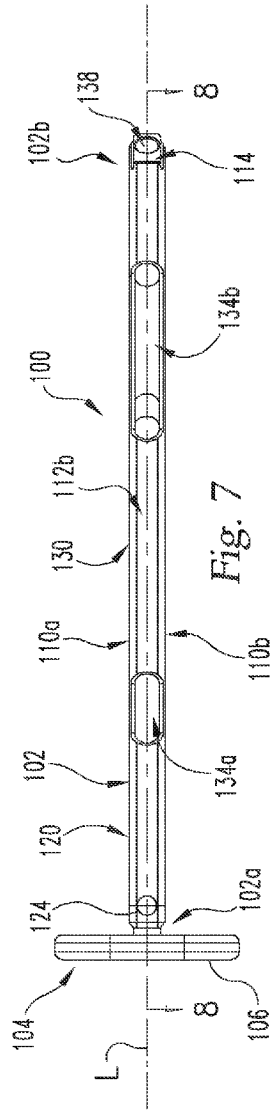
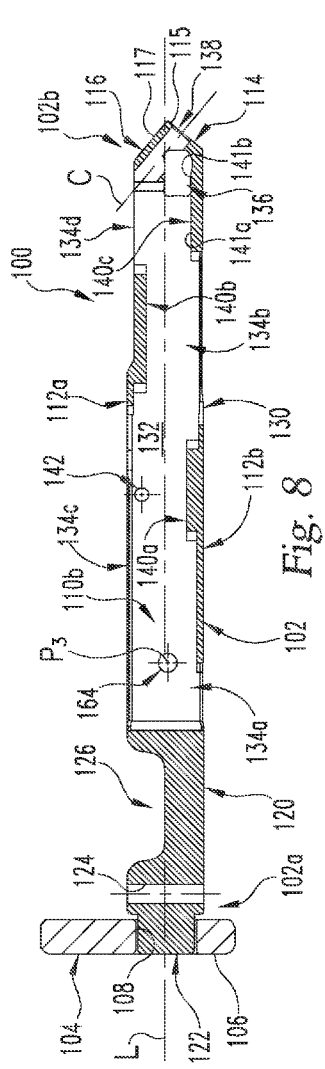

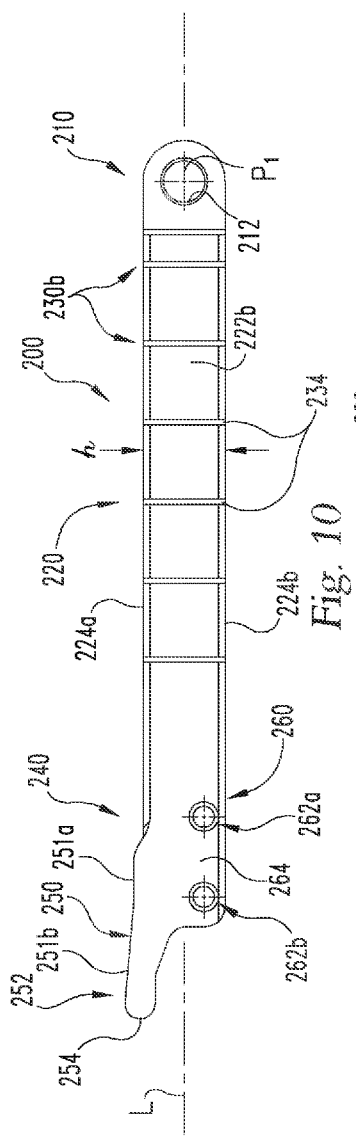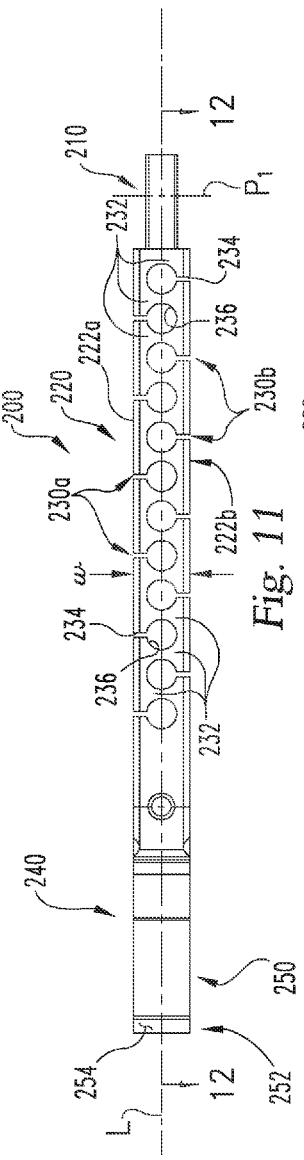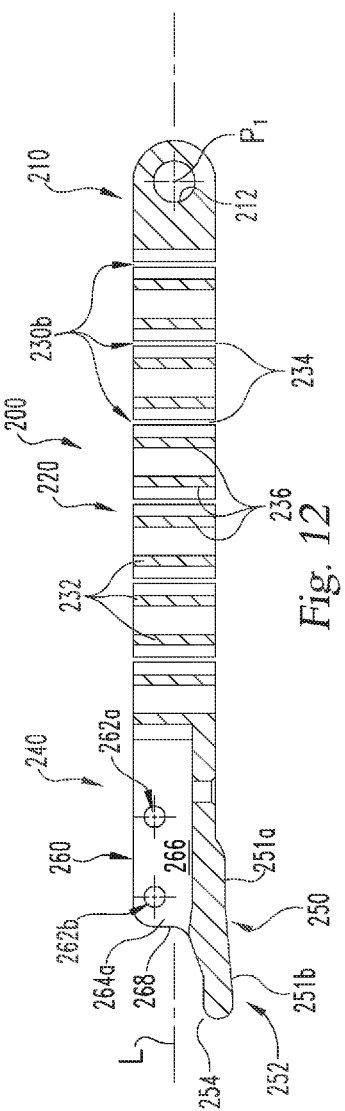

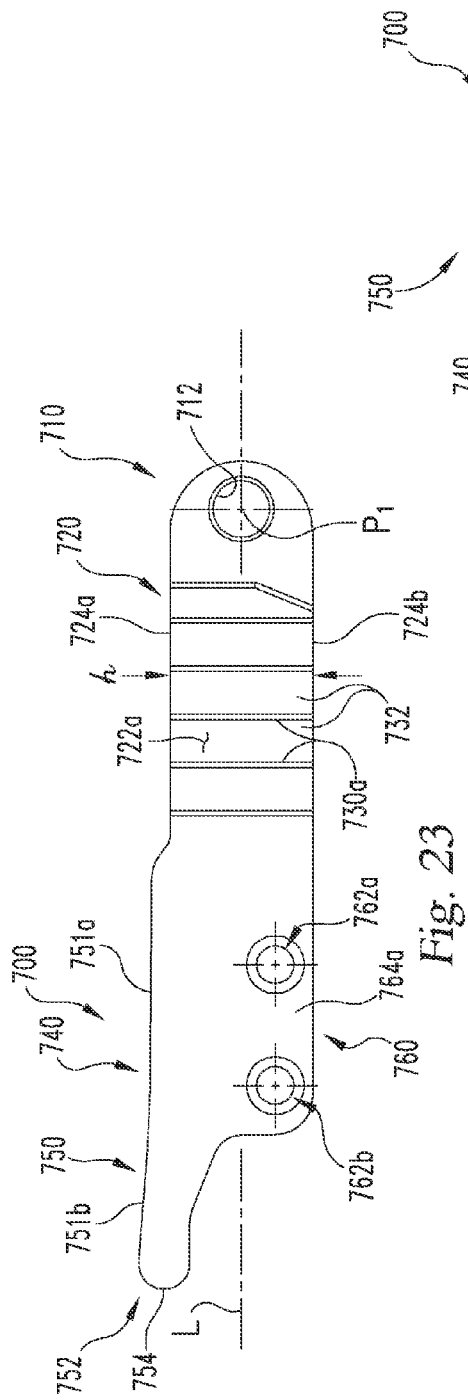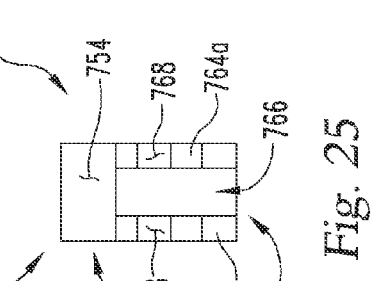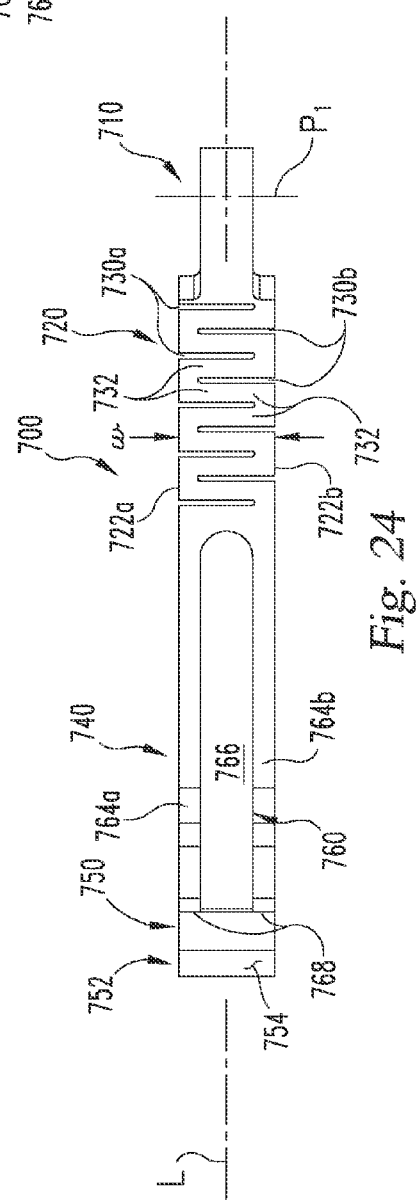

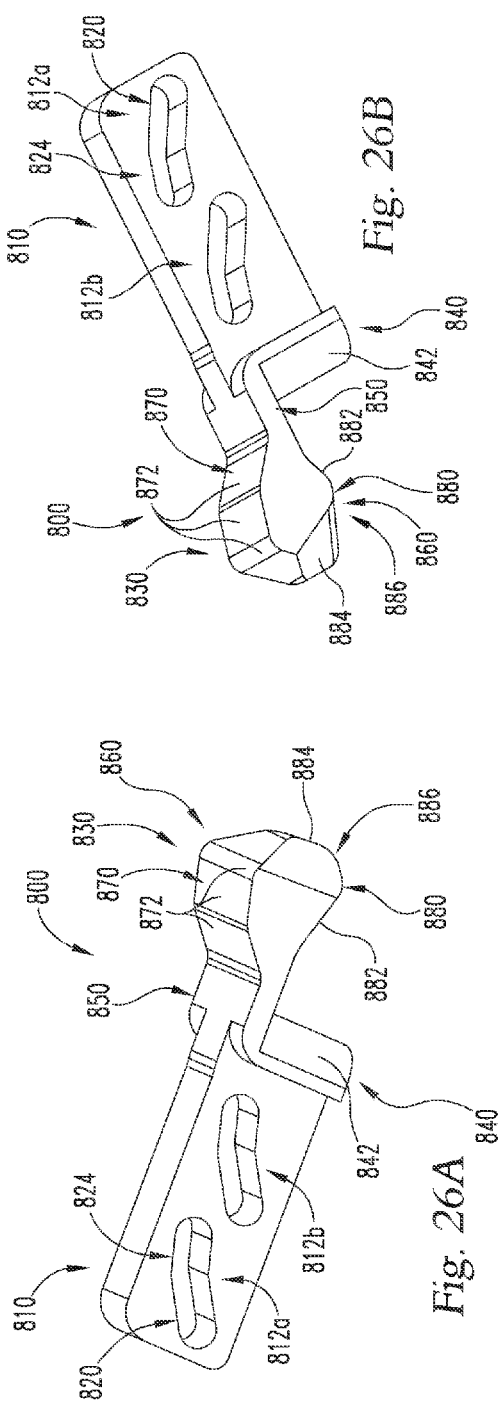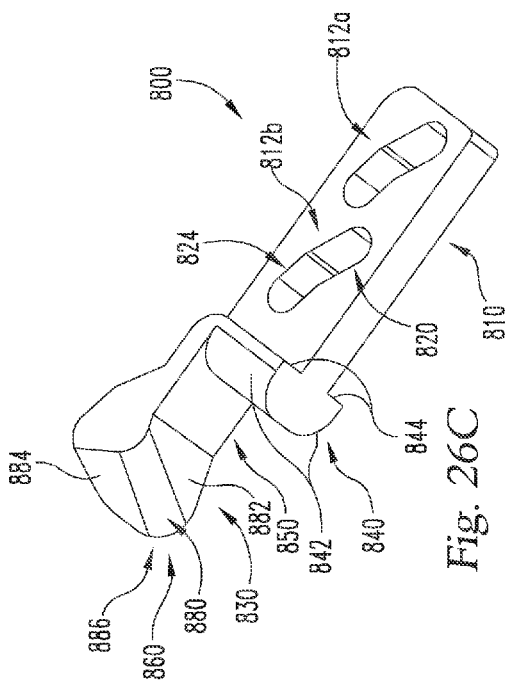

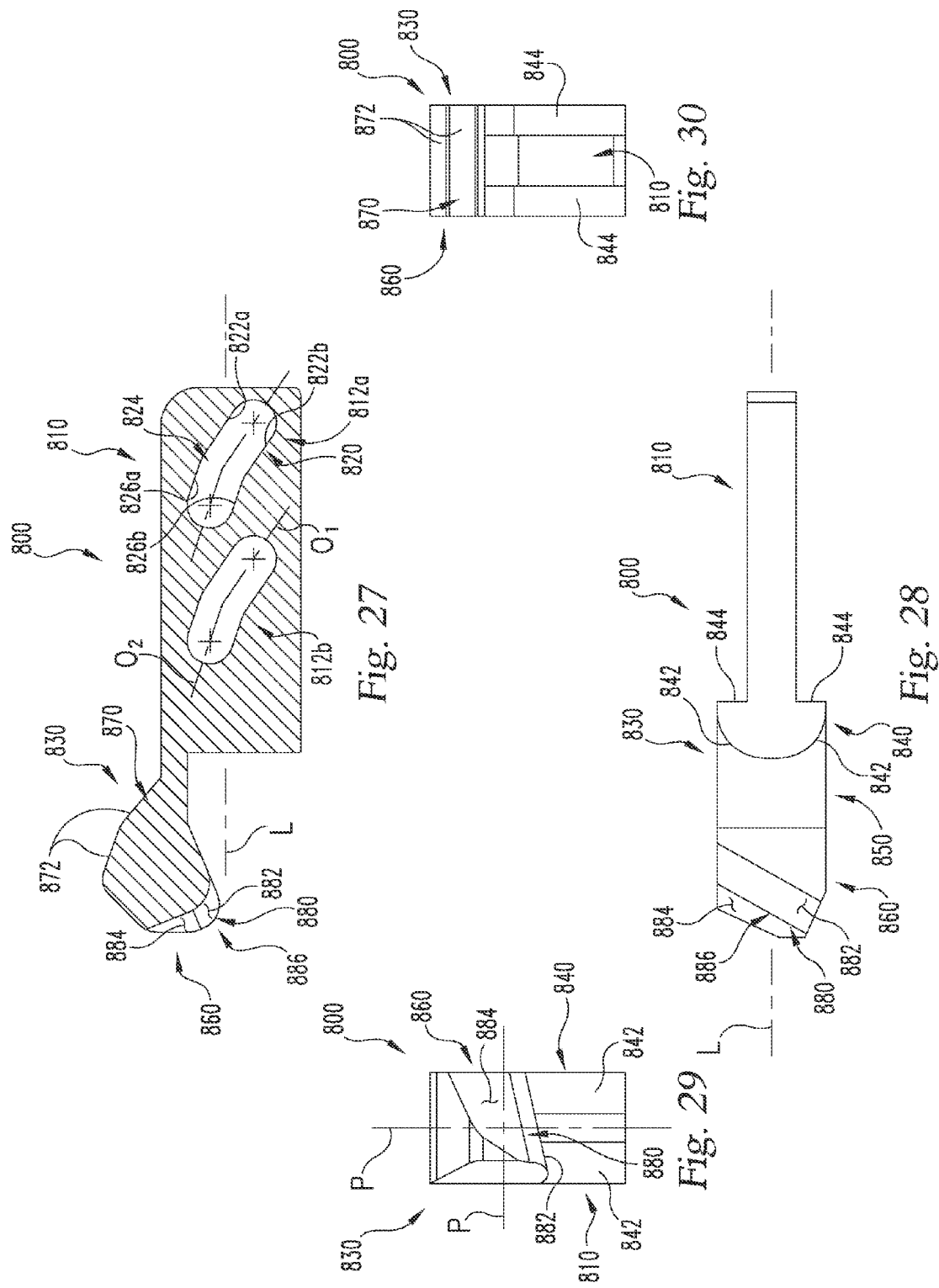

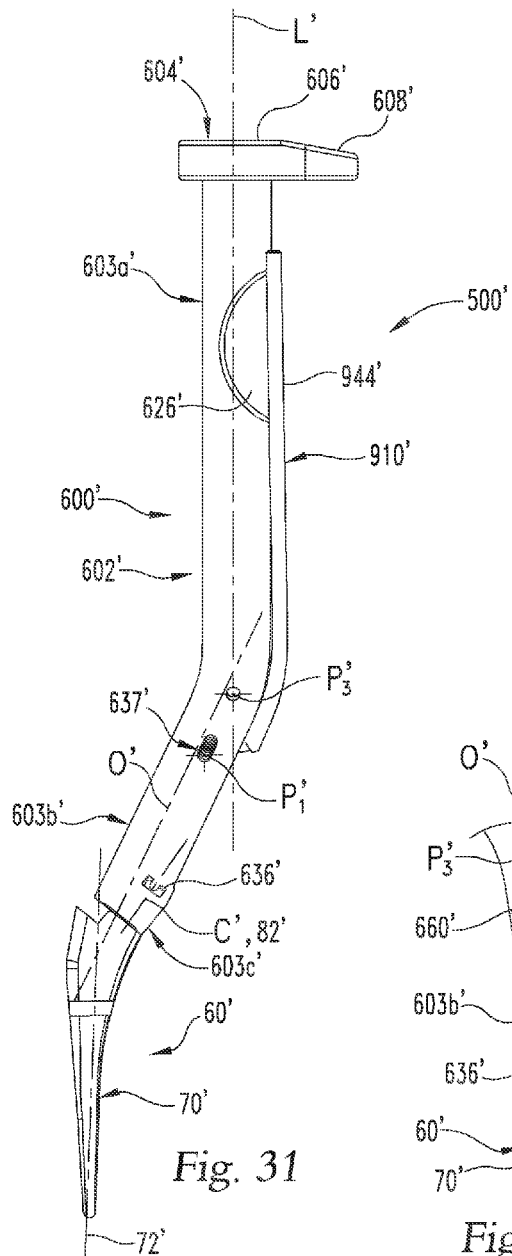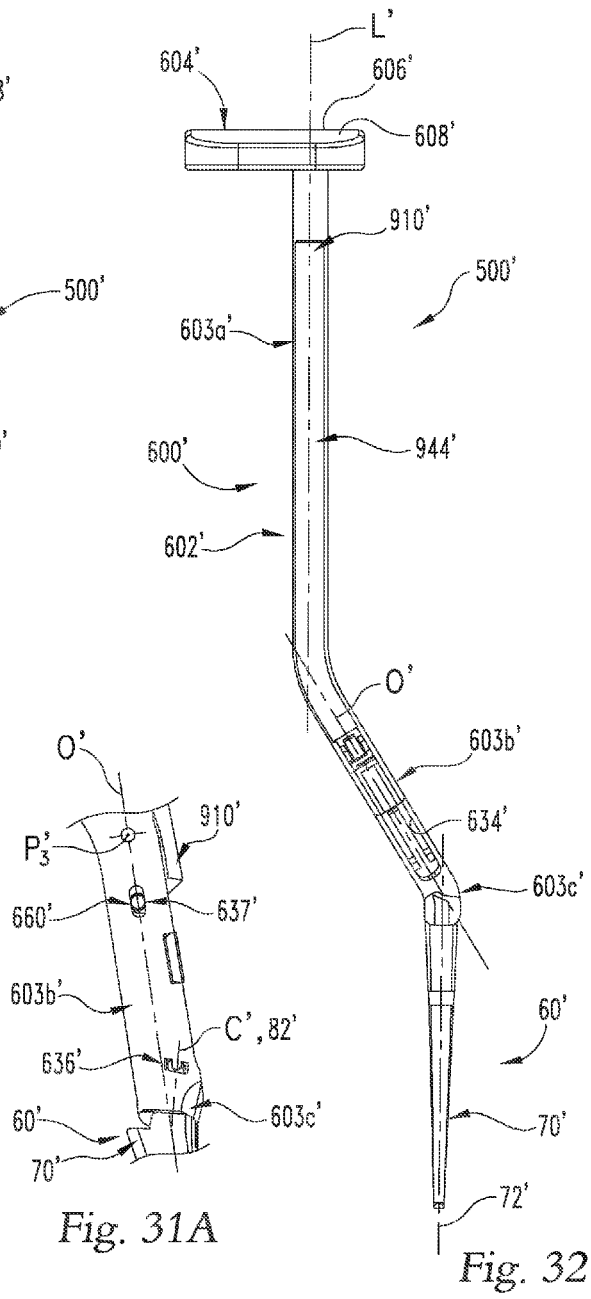

SURGICAL INSTRUMENT HANDLE ASSEMBLY

CROSS REFERENCE TO RELATED APPLICATIONS

The present application claims the benefit of U.S. Provisional Patent Application Ser. No. 61/586,494 filed Jan. 13, 2012, the contents of which are incorporated herein by reference in their entirety.

FIELD OF THE INVENTION

The present invention relates generally to surgical instruments for use in orthopedic surgery, and more particularly but not exclusively relates to a surgical instrument handle assembly configured for releasable connection to orthopedic devices such as orthopedic shaping or cutting members used in total hip arthroplasty.

BACKGROUND

Minimally invasive surgical techniques have become popular in total hip arthroplasty (THA) procedures. Advantages include minimizing soft tissue damage, reducing recovery and healing time, and reducing the length of the patient's hospital stay. One version of a minimally invasive THA techniques is an "anterior approach" or "direct anterior approach" which uses, for example, a portal between the tensor fascia latae muscle and the rectus femoris muscle. An anterior approach can exploit the interval between those muscles for both acetabular and femoral preparation, allow for primary exposure of the hip joint capsule with minimization of muscle damage, limit incision length, and leverage other advantages. However, exposure of the proximal femoral intramedullary canal to prepare the canal for receipt of the femoral stem of a femoral implant can be problematic in a THA procedure using an anterior approach. For example, anatomical features of some patients, such as gut or muscle tissues and/or other anatomic structures, can present problems in accessing and preparing the femoral intramedullary canal via a short surgical incision.

In order to address these concerns, special instrument handles have been developed which may, in some instances, be provided with anterior and/or lateral offsets. Additionally, offset instrument handles reduce mobilization of the targeted bone required to gain access to the femoral intramedullary canal for shaping in preparation for a joint replacement implant such as a femoral stem. This advantage extends to all surgical approaches, and is not limited to a direct anterior approach. A bone shaping or cutting member, such as a broach or rasp, may be connected to the distal end of the instrument handle. The bone shaping member and the distal portion of the instrument handle is inserted through the incision, manipulated to avoid the gut or other anatomic structures by virtue of the anterior and/or lateral offsets, and the bone shaping member is inserted into the intramedullary canal of the femur to shape the canal for subsequent receipt of the femoral stem of a femoral implant.

Current surgical instrument handles configured for connection to bone shaping members are typically large and heavy, and separate instruments may be required for each of the right and left femurs. Consequent issues include those related to, among other things, logistics, inventory requirement, and expense. Additionally, the connection between the instrument handle and the bone shaping member may lack rigidity and may permit a degree of motion therebetween, thereby reducing control of the bone shaping member and also limiting visual and tactile feedback to the surgeon as to the fit of the bone shaping member within the femoral canal which would otherwise provide the surgeon with the ability to estimate the resulting tightness of fit of the femoral stem within the canal and to allow for easier removal of the bone shaping member from the canal subsequent to shaping.

Thus, there remains a need to provide an improved surgical instrument handle assembly for releasable connection to orthopedic shaping or cutting members for use in total hip arthroplasty. The present invention satisfies this need and provides other benefits and advantages in a novel and unobvious manner.

SUMMARY

While the actual nature of the invention covered herein can only be determined with reference to the claims appended hereto, certain forms of the invention that are characteristic of the embodiments disclosed herein are described briefly as follows.

In general, a novel clamping mechanism within a surgical instrument handle assembly is provided for releasable, rotationally and axially rigid connection to orthopedic devices such as orthopedic shaping or cutting members for use in total hip arthroplasty procedures or other orthopedic procedures whereby variation of the design of mating geometry of such a mechanism allows for offset and straight configurations of the surgical instrument handle.

In one form of the invention, a surgical instrument handle assembly is provided for releasable connection to an orthopedic device. The handle assembly includes an elongate shaft including a shaft portion extending generally along a shaft axis and defining an inner chamber at least partially bound by a shaft wall, a clamp element at least partially positioned within the inner chamber and the clamp element including a distal end portion having a bearing portion and a head portion, a compression element at least partially positioned within the inner chamber and including a flexibly elastic portion and a distal engagement portion with the distal engagement portion positioned between the shaft wall and the distal end portion of the clamp element, and an actuator including an initial state and an actuated state with the actuator operatively coupled to the flexibly elastic portion of the compression element and the actuator structured to displace the compression element generally along the inner chamber and to slidably engage the distal engagement portion of the compression element against the bearing portion of the clamp element when transitioned from the initial state toward the actuated state, and an orthopedic device including a body portion and a connection portion extending from the body portion, the connection portion arranged along a connection axis, the connection portion positioned in the inner chamber of the shaft portion and compressingly engaged by the head portion of the clamp element when the actuator is transitioned to the actuated state to thereby rigidly and releasably connect the orthopedic device to the elongate shaft.

In another form of the invention, a surgical instrument handle assembly is provided for releasable connection to an orthopedic device. The handle assembly includes an elongate shaft having an axial shaft portion arranged generally along a longitudinal axis and an offset shaft portion extending from the axial shaft portion and arranged generally along an offset axis with the offset axis defining at least one angular offset relative to the longitudinal axis and the offset shaft portion defining an inner chamber at least partially bound by a shaft wall, a clamp element at least partially positioned within the inner chamber and the clamp element including a distal end portion having a bearing portion and a head portion, a compression element at least partially positioned within the inner chamber and including a flexibly elastic portion and a distal engagement portion with the distal engagement portion positioned between the shaft wall and the distal end portion of the clamp element, and an actuator including an initial state and an actuated state with the actuator operatively coupled to the flexibly elastic portion of the compression element and the actuator structured to displace the compression element generally along the inner chamber and to slidably engage the distal engagement portion of the compression element against the bearing portion of the clamp element when transitioned from the initial state toward the actuated state, and an orthopedic device including a body portion and a connection portion extending from the body portion, the connection portion arranged along a connection axis, the connection portion positioned in the inner chamber of the offset shaft portion and compressingly engaged by the head portion of the clamp element when the actuator is transitioned to the actuated state to thereby rigidly and releasably connect the orthopedic device to the elongate shaft.

It is one object of the present invention to provide an improved surgical instrument handle assembly. Further embodiments, forms, features, aspects, benefits, objects, and advantages of the present invention will become apparent from the detailed description and figures provided herewith.

BRIEF DESCRIPTION OF THE DRAWINGS

FIG. 5 is a side view of one embodiment of a handle for use in association with the surgical instrument handle assembly of FIG. 1.

FIG. 6 is an end view of the handle of FIG. 4.

FIG. 7 is a plan view of the handle of FIG. 4.

FIG. 8 is a cross-section of the handle of FIG. 4, as taken along line 8-8 of FIG. 7.

FIG. 10 is a side view of one embodiment of a compression element for use in association with the linkage assembly of FIG. 9.

FIG. 11 is a plan view of the compression element of FIG. 10.

FIG. 12 is a cross-section of the compression element of FIG. 10, as taken along line 12-12 of FIG. 11.

FIG. 23 is a side view of one embodiment of a compression element for use in association with the surgical instrument handle assembly of FIG. 20.

FIG. 24 is a plan view of the compression element of FIG. 23.

FIG. 25 is an end view of the compression element of FIG. 23.

FIG. 26A is a perspective view of one embodiment of a clamp element for use in association with the surgical instrument handle assembly of FIG. 20.

FIG. 26B is another side perspective view of the clamp element of FIG. 26A.

FIG. 26C is another side perspective view of the clamp element of FIG. 26A.

FIG. 27 is a cross-section of the clamp element of FIG. 26A, as taken along a mid-line of FIG. 26A.

FIG. 28 is a plan view of the clamp element of FIG. 26A.

FIG. 29 is an end view of the clamp element of FIG. 26A.

FIG. 30 is an opposite end view of the clamp element of FIG. 26A.

FIG. 31 is a side view of a surgical instrument handle assembly according to another form of the present invention.

FIG. 31A is an enlarged view of a portion of the surgical instrument handle assembly of FIG. 31.

FIG. 32 is another side view of the surgical instrument handle assembly of FIG. 31.

DESCRIPTION OF THE ILLUSTRATED EMBODIMENTS

Figure 1:
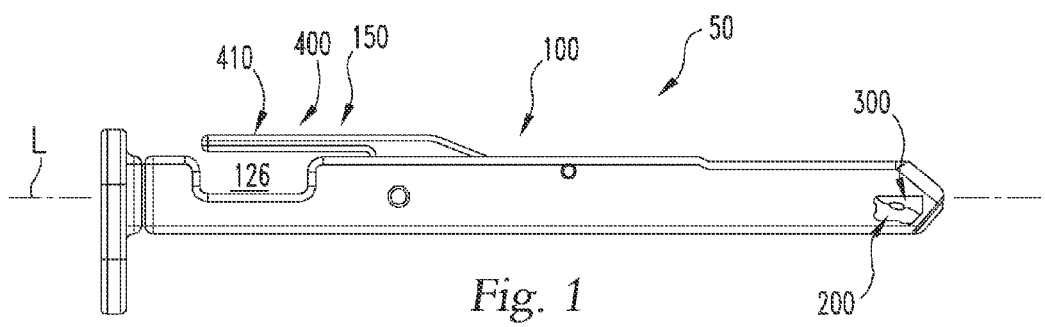
FIG. 1 is a side view of a surgical instrument handle assembly according to one form of the present invention.
Figure 2:
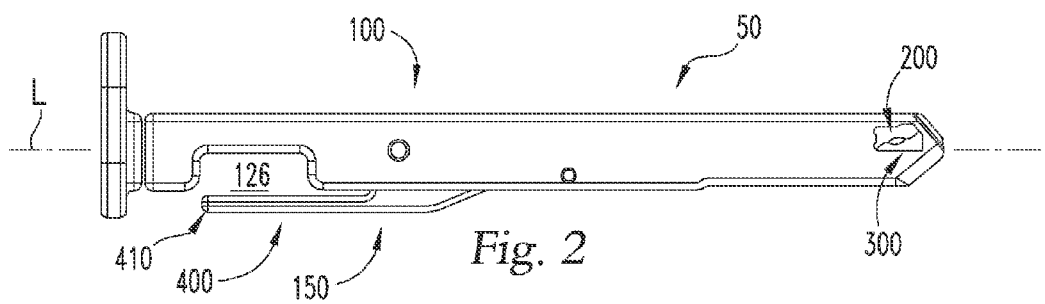
FIG. 2 is an opposite side view of the surgical instrument handle assembly of FIG. 1.
Figure 3:
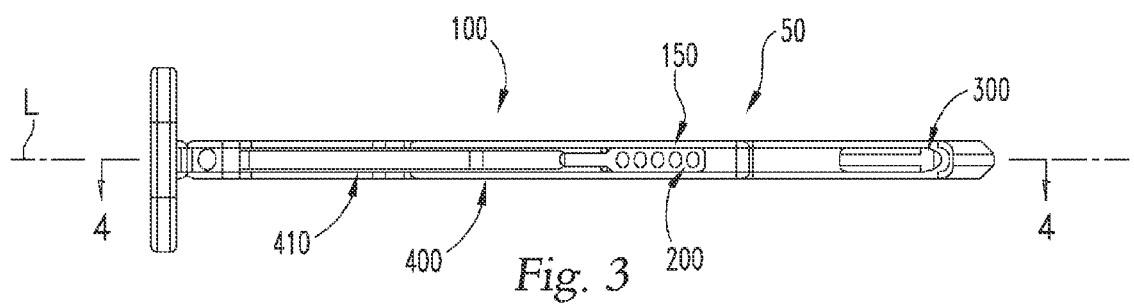
FIG. 3 is a plan view of the surgical instrument handle assembly of FIG. 1.

For the purpose of promoting an understanding of the principles of the present invention, reference will now be made to the embodiments illustrated in the drawings and specific language will be used to describe the same. It will nevertheless be understood that no limitation of the scope of the invention is hereby intended. Any alterations and further modifications in the described embodiments, and any further applications of the principles of the invention as described herein are contemplated as would normally occur to one skilled in the art to which the invention relates.

The following descriptions and illustrations of non-limiting embodiments of the present invention are exemplary in nature, it being understood that the descriptions and illustrations related thereto are in no way intended to limit the inventions disclosed herein and/or their applications and uses. Certain features and details associated with other embodiments of devices and methods that may be used in association with the present invention are found in commonly owned U.S. Pat. No. 7,591,821 issued on Sep. 22, 2009 and commonly owned U.S. patent application Ser. No. 12/263,030 filed on Nov. 20, 2009, the contents of each document incorporated herein by reference in its entirety.

Referring to FIGS. 1-4, shown therein is a surgical instrument 40 according to one form of the present invention that is, in the illustrated embodiment, configured for preparation of the intramedullary canal of a femur in a total hip replacement surgery. However, it should be understood that the surgical instrument 40 may be used in association with other orthopedic surgeries or procedures associated with the hip, surgeries or procedures associated with other joints such as, for example, the shoulder and knee, or surgeries involving bones in addition to the femur. The surgical instrument 40 generally includes a surgical instrument handle assembly 50 that is rigidly and releasably connectable to an orthopedic device 60 (FIGS. 4A and 4B) such as, for example, an orthopedic shaping or cutting member. The components of the surgical instrument handle assembly 50 and the orthopedic device 60 may be formed of any suitable material having appropriate strength, manufacturability, autoclavability, and other desired performance factors. In one embodiment, the components of the handle assembly 50 and the orthopedic device 60 are formed of biocompatible stainless steel and/or titanium. However, it should be understood that other metallic materials, composite materials, and/or plastic materials may be used.

In the illustrated embodiment, the shaping/cutting member 60 is configured as an orthopedic broach. However, other types and configurations of shaping/cutting members are also contemplated for use in association with the present invention including, for example, a rasp, an osteotome, a reamer, a sawblade, a bit, a graft impaction member, or other orthopedic devices suitable for shaping or cutting bone. In other embodiments, instead of a shaping/cutting member 60, the handle assembly 50 may be used to rigidly and releasably connect to other orthopedic devices such as, for example, an intramedullary implant (i.e., a femoral stem) via direct connection of the device with the handle assembly 50 or via the use of an intermediate adaptor.

Figure 4:
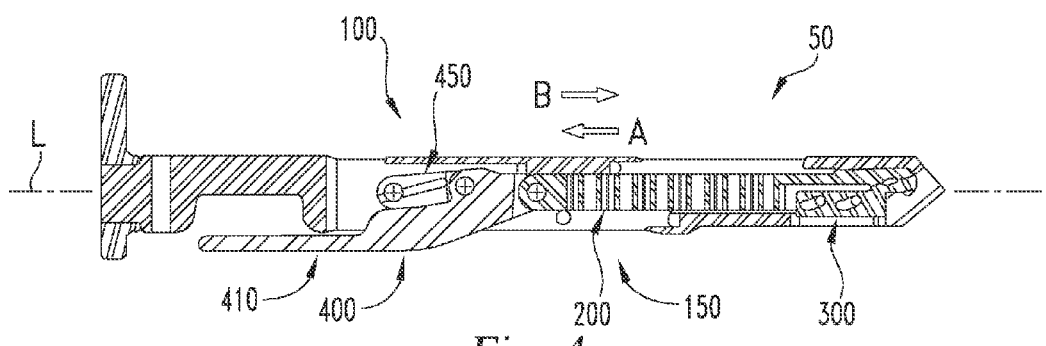
FIG. 4 is a cross-section of the surgical instrument handle assembly of FIG. 1, as taken along line 4-4 of FIG. 3.
Figure 4A:
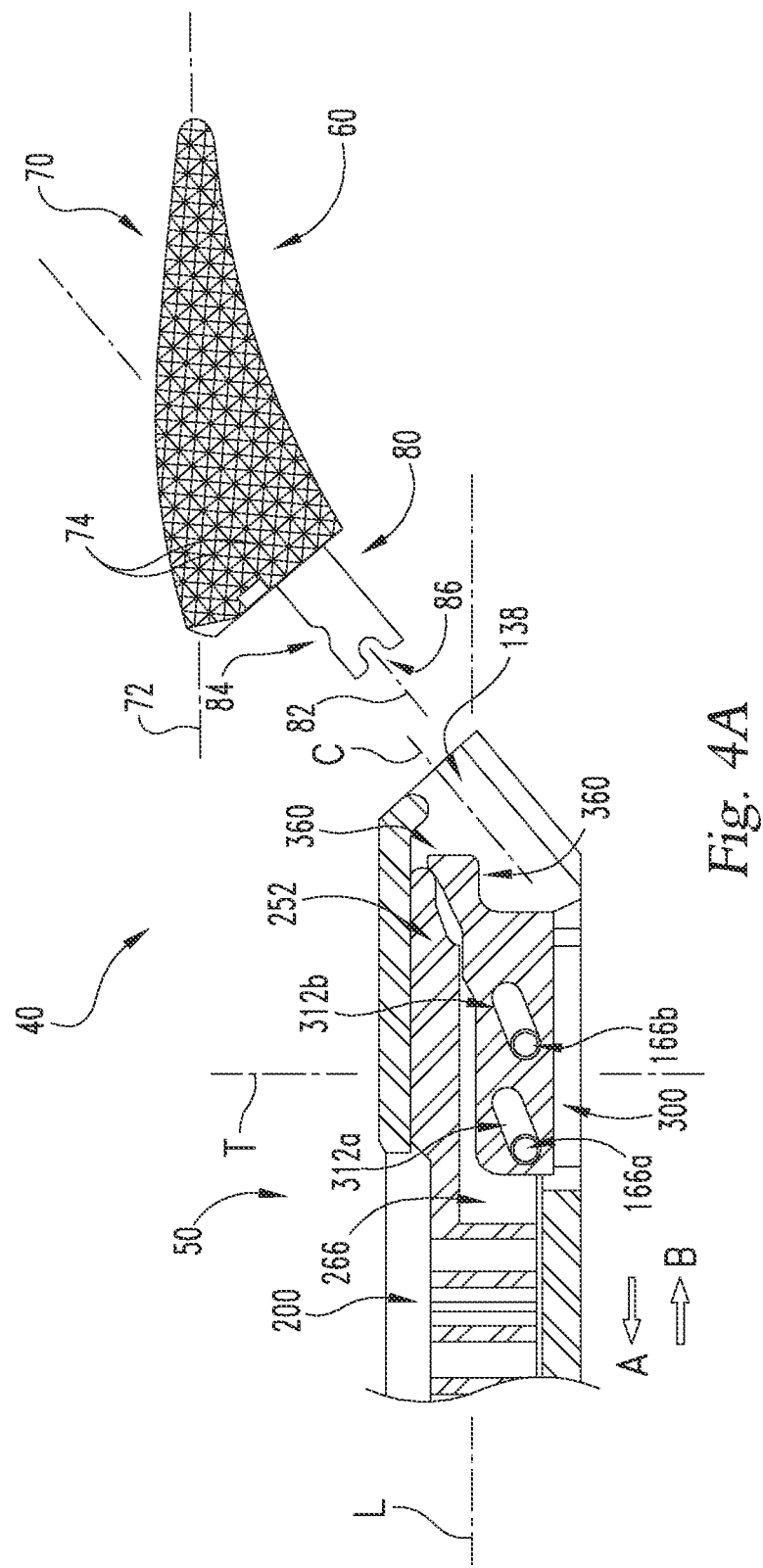
FIG. 4A is an enlarged view of a distal portion of the surgical instrument handle assembly of FIG. 4, as positioned in an unlocked configuration for receipt of an orthopedic shaping member.
Figure 4B:
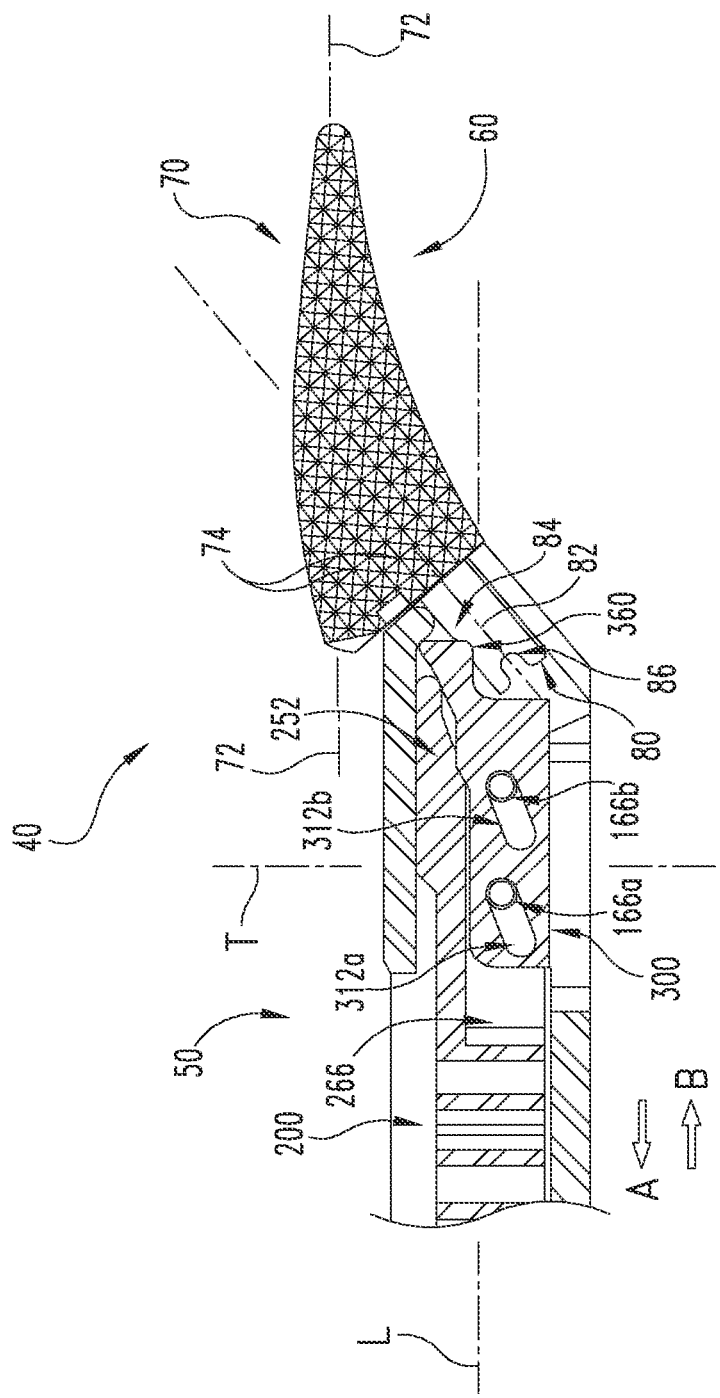
FIG. 4B is an enlarged view of a distal portion of the surgical instrument handle assembly of FIG. 4, as positioned in a locked configuration with the orthopedic shaping member engaged to the handle assembly.

As shown in FIGS. 4A and 4B, in the illustrated embodiment, the broach 60 includes a shaping body portion 70 and a connection post or stem portion 80 extending therefrom. In one embodiment of the broach 60, the shaping body 70 has a shape that generally matches that of a femoral implant to be subsequently inserted into the femoral medullary canal subsequent to preparation of the canal via the instrument 40. The shaping body 70 typically includes a pair of opposite surfaces arranged substantially parallel to and spaced apart from a longitudinal axis 72 extending through the approximate center of the shaping body 70. The parallel surfaces are typically provided with a plurality of cutting teeth 74 or other cutting/shaping features configured to remove material from the femoral intramedullary canal to shape the canal. Although a particular type and configuration of the shaping body 70 has been illustrated and described herein, it should be understood that other types and configurations are also contemplated as would occur to one having ordinary skill in the art.

In the illustrated embodiment of the broach 60, the connection post or stem 80 extends generally along a connection axis 82 and defines one or more connection features configured for mating engagement with corresponding connection features defined by the handle assembly 50 to aid in rigidly connecting the broach 60 to the handle assembly 50, the details of which will be set forth below. In one embodiment, the connection post 80 is provided with two such connection features including a first notch or groove 84 extending transversely into a side of the post 80 (i.e., in a direction transverse to the connection axis 82), and a second notch or groove 86 extending axially into an end of the post 80 (i.e., in a direction generally parallel with the connection axis 82). However, it should be understood that the connection post 80 may be provided with other types and configurations of connection features and may be provided as a negative connection feature (e.g., a notch, groove or opening formed in the post 80) and/or as a positive connection feature (e.g., a projection, extension or ridge extending from the post 80). In one embodiment, the transverse notch 84 has a V-shaped configuration and the axial notch 86 has a semi-circular configuration. However, other shapes and configurations of the notches 84, 86 are also contemplated. Additionally, in the illustrated embodiment, the connection axis 82 of the connection post 80 is arranged at an oblique angle relative to the longitudinal axis 72 of the shaping body 70. However, other configurations are also contemplated wherein the connection axis 82 and the longitudinal axis 72 are arranged generally parallel with one another. Although a particular type and configuration of the connection post 80 has been illustrated and described herein, it should be understood that other types and configurations are also contemplated as would occur to one having ordinary skill in the art.

Figure 9:
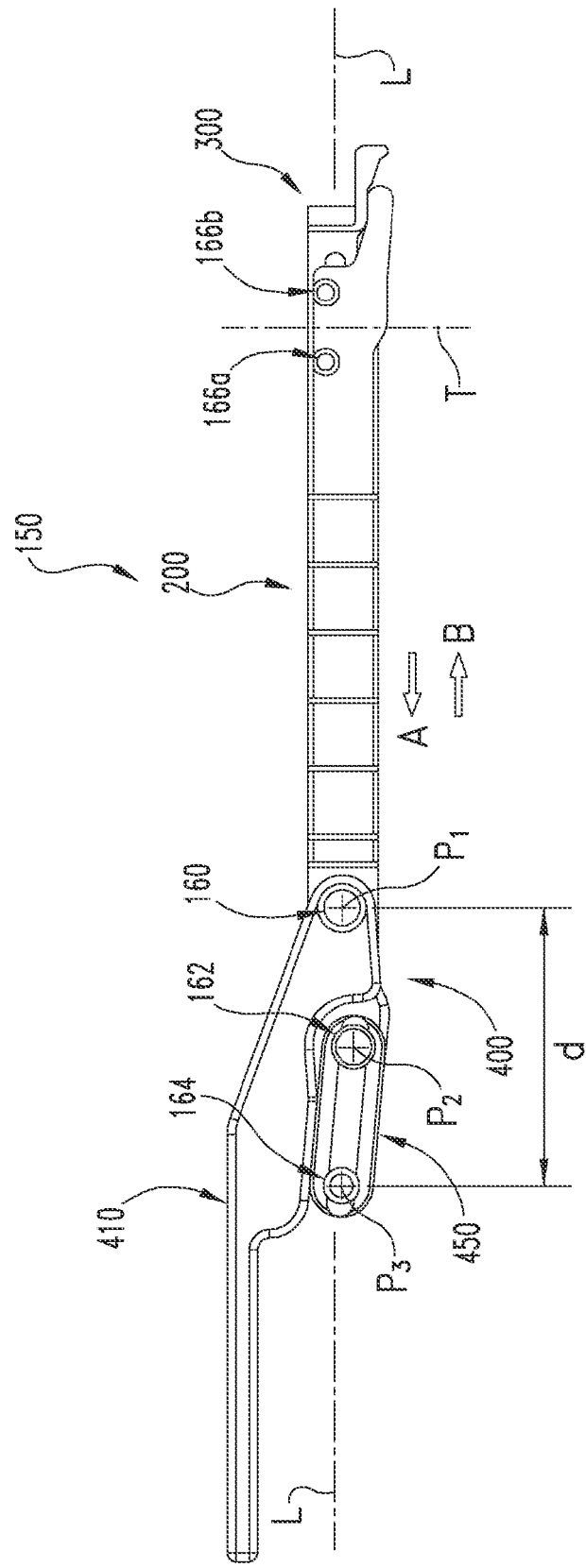
FIG. 9 is a side view of one embodiment of a linkage assembly for use in association with the surgical instrument handle assembly of FIG. 1.

Referring collectively to FIGS. 1-4, the surgical instrument handle assembly 50 extends along a longitudinal axis L and generally includes an axial handle 100 and a linkage assembly 150 movably connected to the axial handle 100 and at least partially positioned within an interior region of the axial handle 100. Referring to FIGS. 4 and 9, in the illustrated embodiment, the linkage assembly 150 generally includes a compression element 200, a clamp element 300, and an actuator mechanism 400. In the illustrated embodiment, the actuator mechanism 400 is a toggle-type actuator and generally includes a toggle handle or lever arm 410 and a toggle link or bar 450. As will be discussed in greater detail below, actuation of the actuator mechanism 400 serves to displace the compression element 200 relative to the clamp element 300, which in turn compresses a distal portion of the clamp element 300 in a transverse direction against the connection post 80 of the broach 60 to securely capture the post 80 between the clamp element 300 and a distal portion of the axial handle 100, thereby rigidly and releasably connecting the broach 60 to the handle assembly 50.

Referring to FIGS. 5-8, shown therein are further details regarding the axial handle 100. In the illustrated embodiment, the axial handle 100 generally includes an elongate shaft 102 having a proximal end portion 102a and a distal end portion 102b, and a strike plate or impaction platform 104 attached to the proximal end portion 102a of the elongate shaft 102. In one embodiment, the impaction platform 104 is formed separately from the elongate shaft 102 and is attached thereto by any suitable attachment technique such as, for example, welding or fastening. However, other embodiments are also contemplated where the impaction platform 104 and the elongate shaft 102 are formed as a unitary, monolithic structure.

In one embodiment, the elongate shaft 102 has a generally linear configuration extending axially along the longitudinal axis L. However, other configurations are also contemplated wherein the elongate shaft 102 may have a curved configuration, a curvi-linear configuration, and/or an offset configuration including, for example, an anterior offset, a lateral offset, or a dual-offset including both an anterior offset and a lateral offset. Other suitable configurations of the elongate shaft 102 are also contemplated as would occur to one of ordinary skill in the art. In a further embodiment, the impaction platform 104 has a square or rectangular configuration and defines a generally flat/planar proximally-facing impact or strike surface 106 extending along a plane arranged generally perpendicular to the longitudinal axis L. The impact surface 106 provides an enlarged surface area on which the surgeon may strike the handle assembly 50 to enhance transmission of an impaction force through the handle assembly 50 to the shaping/cutting member 60 connected to the distal end portion 102b of the elongate shaft 102.

Although the impaction platform 104 and the impact surface 106 have been illustrated and described as having a particular shape and configuration, it should be understood that other shapes and configurations are also contemplated. For example, in other embodiment, the impact surface 106 may be provided with one or more angled or tapered regions extending along planes arranged oblique to the longitudinal axis L to provide the surgeon with the ability to apply an oblique impaction force to the axial handle 100 in a direction that is not perpendicular to the longitudinal axis L. Additionally, the impact surface 106 may be provided with a non-planar configuration including curved or rounded configurations or curvi-linear configurations. As should be appreciated, the elongate shaft 102 provides the surgeon with a structure to grip and manipulate, while the impaction platform 104 provides the surgeon with a structure that may be impacted or stricken with an impaction/striking device such as a hammer, a mallet, or other suitable devices. In other embodiments, the impaction platform 104 may alternately be configured as an integral impact device such as a slap hammer. In still other embodiments, the axial handle 100 need not necessarily include an impaction platform 104.

In the illustrated embodiment, the elongate shaft 102 has a generally rectangular outer transverse cross-section defined by a pair of opposite longitudinal side walls 110a, 110b and a pair of opposite longitudinal edge walls 112a, 112b. The elongate shaft 102 further includes a first distal end wall 114 defining a first distal end surface 115 extending at an oblique angle relative to the longitudinal axis L, and a second distal end wall 116 defining a second distal end surface 117 extending substantially normal or perpendicular to the first distal end surface 115. Additionally, the elongate shaft 102 generally includes a substantially solid proximal region 120 extending distally from the impaction platform 104, and a tubular region 130 extending distally from the proximal region 120 to the distal end portion 102b. The substantially solid proximal region 120 of the elongate shaft 102 provides added strength and structural integrity to absorb and transmit the impact/strike force applied to the impaction platform 104. The tubular region 130 provides the elongate shaft 102 with a hollow interior to house the components of the linkage assembly 150. However, it should be understood that other suitable shapes and configurations of the elongate shaft 102 are also contemplated.

The substantially solid proximal region 120 of the elongate shaft 102 includes a proximal stem 122 positioned within a corresponding opening 108 formed in the impaction platform 104 to strengthen the interconnection between the impaction platform 104 and the elongate shaft 102. The proximal region 120 further includes a passage or opening 124 extending transversely therethrough between the longitudinal edge walls 112a, 112b, and a recess or indentation 126 defined along the longitudinal edge wall 112a and extending into the longitudinal side walls 110a, 110b. The transverse recess 126 is sized and shaped to provide access to the end portion of the toggle handle 410 (FIGS. 1 and 2) such that the lever portion of the toggle handle 410 may be readily grasped and manipulated by one or more fingers and/or the thumb of the surgeon.

In the illustrated embodiment, the tubular region 130 of the elongate shaft 102 defines a hollow interior or inner chamber 132 (FIG. 8), a number of slotted openings 134a-134d extending transversely through the longitudinal edge walls 112a, 112b and into communication with the hollow interior 132, a window 136 extending transversely through the longitudinal side walls 110a, 110b adjacent a distal region of the elongate shaft 102 and into communication with the hollow interior 132, and a distal passage 138 extending through the distal end wall 114 and into communication with the hollow interior 132. The slotted openings 134a-134d and the window 136 provide ready access to the components contained within the hollow interior 132, aid in manufacturing, assembly and/or maintenance of the handle assembly 50, facilitate cleaning and/or sterilization of the handle assembly 50, and/or may provide direct visualization of the components contained within the hollow interior 132 to verify proper operation. The distal passage 138 is arranged generally along a connection axis C and is sized and shaped for receipt of the connection post 80 of the broach 60 therein (FIGS. 4A/4B). In one embodiment, the connection axis C of the distal passage 138 is arranged substantially normal or perpendicular to the distal end surface 115 of the distal end wall 114, and is also arranged at an oblique angle α of approximately forty (40) degrees relative to the longitudinal axis L. However, other orientations of the distal passage 138 are also contemplated. Additionally, in the illustrated embodiment of the elongate shaft 102, the slotted openings 134a-134d and the visualization window 136 each have a generally rectangular shape, and the distal passage 138 has a generally circular shape. However, other shapes and configurations of the slotted openings 134a-134d, the visualization window 136, and the distal passage 138 are also contemplated.

Referring specifically to FIG. 8, in the illustrated embodiment, the elongate shaft 102 is provided with a number of raised lands or plateaus 140a-140c extending inwardly into the hollow interior 132 from inner surfaces of the longitudinal edge walls 112a, 112b. The raised lands or plateaus 140a-140c define generally flat/planar bearing surfaces arranged generally parallel with the longitudinal axis L which may serve to guide the compression element 200 and/or the clamp element 300 in a direction generally parallel with the longitudinal axis L upon actuation of the actuator mechanism 400. Additionally, in the illustrated embodiment, a guide pin 142 and a pivot pin 164 each extend across the hollow interior 132 between the longitudinal side walls 110a, 110b. The guide pin 142 is positioned generally opposite the plateau 140a and aids in guiding the compression element 200 in a direction generally parallel with the longitudinal axis L upon actuation of the actuator mechanism 400. Other features or structures may also be provided to add strength and structural integrity to the compression element 200 and to further aid in guiding the compression element 200 in a direction generally parallel with the longitudinal axis L. For example, an end portion or head of the pivot pin 160 (FIG. 9) that pivotally connects the compression element 200 with the toggle handle 410 may be slidably displaced along an axial slot or groove formed in one or both of the shaft side walls 110a, 110b during axial displacement of the compression element 200. As will be discussed in greater detail below, the pivot pin 164 is arranged generally along a pivot axis $P_3$ and is sized and configured for receipt within an opening in a proximal portion of the toggle link 450 to permit the toggle link 450 to pivot about the pivot pin 164 upon actuation of the actuator mechanism 400 while preventing axially displacement of the toggle link 450 along the longitudinal axis L.

Referring to FIG. 9, shown therein are further details regarding the linkage assembly 150. As indicated above, the linkage assembly 150 generally includes a compression element 200, a clamp element 300, and an actuator mechanism 400 comprised of a toggle handle 410 and a toggle link 450. In the illustrated embodiment, the components of the linkage assembly 150 are interconnected via a series of pins or shafts. Specifically, a proximal portion of the compression element 200 is pivotally connected to a first portion of the toggle handle 410 via a first pivot pin 160 extending along a first pivot axis $P_1$ to permit pivotal movement of the toggle handle 410 relative to the compression element 200 about the first pivot axis $P_1$. Additionally, a second portion of the toggle handle 410 is pivotally connected to a distal portion of the toggle link 450 via a second pivot pin 162 extending along a second pivot axis $P_2$ to permit pivotal movement of the toggle handle 410 relative to the toggle link 450 about the second pivot axis $P_2$. As indicated above, a proximal portion of the toggle link 450 is pivotally connected to the axial handle 100 via a third pivot pin 164 extending along a third pivot axis $P_3$ to permit pivotal movement of the toggle link 450 relative to the axial handle 100 about the third pivot axis $P_3$ while preventing axially displacement of the toggle link 450 along the longitudinal axis L.

Furthermore, a distal portion of the compression element 200 is slidably attached to the clamp element 300 via a pair of dowel pins 166a, 166b to permit a degree of relative axial movement of the compression element 200 relative to the clamp element 300 along a first vector arranged generally parallel with the longitudinal axis L, as well as a degree of relative transverse movement of the clamp element 300 relative to the compression element 200 generally along a second vector arranged generally parallel with the transverse axis T, further details of which will be set forth below. It should be appreciated that in one embodiment, movement of the compression element 200 relative to the clamp element 300 along the first and second vectors may occur simultaneously as a composite movement extending at an oblique angle relative to the longitudinal axis L and the transverse axis T. However, other embodiments and other types of movement between the compression element 200 and the clamp element 300 are also contemplated, including sequential movement of the compression element 200 relative to the clamp element 300 along the first and second vectors or directions of travel.

As should be appreciated, pivotal movement of the toggle handle 410 about the pivot axis $P_1$ in an outward direction away from the longitudinal axis L correspondingly pivots the toggle link 450 about the pivot axis $P_3$ in an outward direction away from the longitudinal axis L. This outward pivotal movement of the toggle handle 410 and the toggle link 450 reduces the distance d between the pivot axes $P_1$ and $P_3$. Since the proximal portion of the toggle link 450 remains in a stationary axial position (via the pivot pin 164 attached to the axial handle 100), outward pivotal movement of the toggle handle 410 and the toggle link 450 pulls the compression element 200 in a proximal direction which in turn proximally displaces the compression element 200 in the direction of arrow A generally along the longitudinal axis L. Conversely, pivotal movement of the toggle handle 410 about the pivot axis $P_1$ in an inward direction toward the longitudinal axis L correspondingly pivots the toggle link 450 about the pivot axis $P_3$ in an inward direction toward the longitudinal axis L. This inward pivotal movement of the toggle handle 410 and the toggle link 450 increases the distance d between the pivot axes $P_1$ and $P_3$, which in turn pushes the compression element 200 in a distal direction which in turn distally displaces the compression element 200 in the direction of arrow B generally along the longitudinal axis L. As will be discussed in greater detail below, the proximal/distal movement of the compression element 200 in the direction of arrows A/B serves to transition the clamp element 300 between unlocked and locked configurations.

Referring to FIGS. 10-12, shown therein are further details regarding the compression element 200. In the illustrated embodiment, the compression element 200 has a rod or shaft-like configuration extending along the longitudinal axis L. Additionally, the compression element 200 generally includes a proximal connection portion or pivot plate member 210 configured for pivotal connection with the toggle handle 410, a compression portion or spring-like member 220 having spring-like characteristics exhibiting flexibly elastic resiliency along the longitudinal axis L, and a distal engagement portion or pusher member 240 configured for movable/slidable engagement with the clamp element 300 to force the clamp element 300 into compressed engagement against the connection post 80 of the broach 60 to rigidly and releasably connect the broach 60 to the handle assembly 50. In the illustrated embodiment, the proximal connection portion 210, the compression portion 220, and the distal engagement portion 240 are integral with one another to provide the compression element 200 as a single-piece monolithic structure. However, in other embodiments, one or more portions of the compression element 200 may be provided as separate members that are assembled together to form a multi-piece compression element 200.

In the illustrated embodiment, the proximal connection portion or pivot plate member 210 of the compression element 200 has a plate-like configuration defining an opening 212 extending therethrough in a direction transverse to the longitudinal axis L. The opening 212 is positioned along the pivot axis $P_1$ and is sized to receive the pivot pin 160 therein to pivotally connect the compression element 200 to the toggle handle 410 (FIG. 9). Although a particular configuration of the proximal connection portion 210 has been illustrated and described herein, it should be understood that other suitable configurations are also contemplated.

In the illustrated embodiment, the compression portion or spring member 220 of the compression element 200 has a substantially rectangular outer transverse cross-section including opposite first and second longitudinal sides 222a, 222b defining an overall width dimension w therebetween, and opposite first and second longitudinal edges 224a, 224b defining an overall height dimension h therebetween. As indicated above, the compression portion 220 has spring-like characteristics exhibiting flexibly elastic resiliency along the longitudinal axis L. The spring-like characteristics are provided by a first series of slots or slits 230a extending from the first longitudinal side 222a and transversely across a portion of the overall width dimension w and along the entire overall height dimension h, and a second series of slots or slits 230b extending from the second longitudinal side 222b and transversely across a portion of the overall width dimension w and along the entire overall height dimension h.

In the illustrated embodiment, the slits 230a, 230b are offset from one another along the length of the compression portion 220 in an alternating manner so as to define a relatively narrow strip of material 232 extending along the longitudinal axis L in an undulating or sinusoidal configuration. In one embodiment, the slits 230a, 230b extend across greater than one-half of the overall width dimension w, and in a further embodiment extend across approximately three-quarters of the overall width dimension w. However, other embodiments are also contemplated where the slits 230a, 230b extend across other portions of the overall width dimension w. Additionally, in the illustrated embodiment, the slits 230a, 230b each include a relatively narrow region 234 extending from the respective side 222a, 222b which opens into an enlarged end region 236 to provide additional flexibility and elasticity to the compression portion 220. In one embodiment, the narrow region 234 of the slits 230a, 230b has a substantially rectangular configuration and the enlarged end region 234 of the slits 230a, 230b has a substantially circular or ovular/elliptical configuration. However, other suitable shapes and configurations of the slits 230a, 230b are also contemplated. As should be appreciated, the slits 230a, 230b provide the compression portion 220 with spring-like characteristics including flexibly elastic resiliency along the longitudinal axis L and to a lesser degree in directions transverse to the longitudinal axis L. Although a particular configuration of the compression portion 220 has been illustrated and described herein, it should be understood that other suitable spring-like configurations are also contemplated.

In the illustrated embodiment, the distal engagement portion or pusher member 240 of the compression element 200 generally includes an engagement plate portion 250 extending along the longitudinal axis L, and a connection portion 260 extending substantially perpendicularly from the engagement plate portion 250.

The engagement plate portion 250 includes a distal end portion 252 defining a distal engagement surface 254. In one embodiment, the distal engagement surface 254 has a curved or semi-circular configuration. However, other suitable shapes and configurations of the distal engagement surface 254 are also contemplated. Additionally, in the illustrated embodiment, the engagement plate portion 250 defines a first outer surface portion 251a arranged generally parallel with the longitudinal axis L, and a second outer surface portion 251b extending from the first outer surface portion 251a and defining a relatively small outward taper or incline extending toward the distal end portion 252. The tapered outer surface portion 251b is engagable with a corresponding angled/undercut surface portion 141b formed along the raised land or plateau 140c adjacent the distal end of the elongate shaft 102 (FIG. 8) when the linkage assembly 150 is positioned in a fully extended or locked state. Such engagement provides for rigid and secure engagement between the compression element 200 and the elongate shaft 102 and between the compression element 200 and the clamp element 300 when the handle assembly 50 is positioned in the fully extended/locked state to substantially prevent motion therebetween, which in turn provides for rigid and secure locked engagement between the handle assembly 50 and the connection post 80 of the broach 60.

In the illustrated embodiment, the connection portion 260 is configured as a U-shaped clevis including a pair of plates or flanges 264a, 264b extending transversely from the engagement plate portion 250 and spaced apart from one another to define a yoke or gap 266 therebetween sized for receipt of a portion of the clamping element 300 therein. The flanges 264a, 264b in turn define a pair of generally circular openings 262a, 262b that are axially offset from one another along the longitudinal axis L. The pair of openings 262a, 262b are sized and shaped to receive the dowel pins 166a, 166b therein, respectively, which are in turn positioned within corresponding slotted openings in the clamp element 300 to thereby movably and slidably connect the compression element 200 with the clamp element 300 with a portion of the clamp element 300 being guidingly displaced within the gap 266 between the flanges 264a, 264b. Positioning of a portion of the clamp element 300 within the gap 266 between the flanges 264a, 264b of the compression element 200 also serves to increase the strength and structural integrity of the slidable interconnection between the compression element 200 and the clamp element 300. Although a particular configuration of the distal engagement portion 240 has been illustrated and described herein, it should be understood that other suitable configurations are also contemplated.

Figure 13:
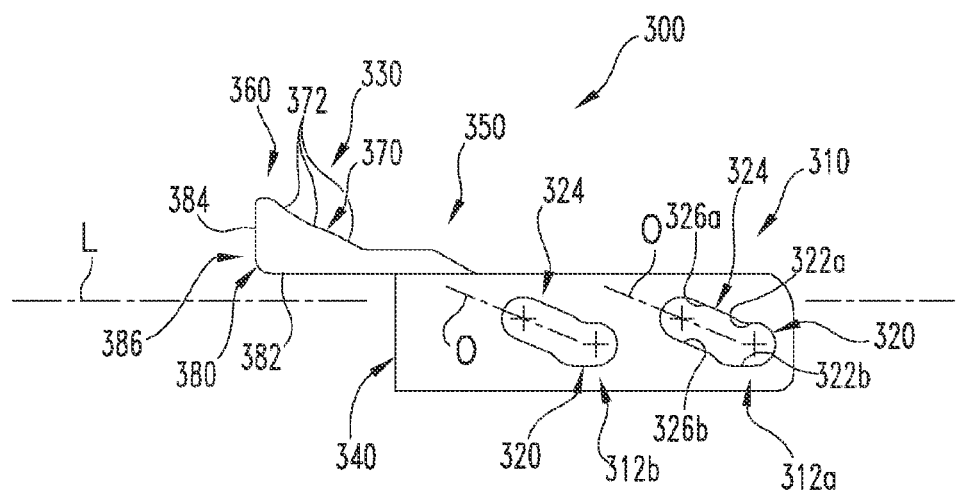
FIG. 13 is a side view of one embodiment of a clamp element for use in association with the linkage assembly of FIG. 9.
Figure 14:
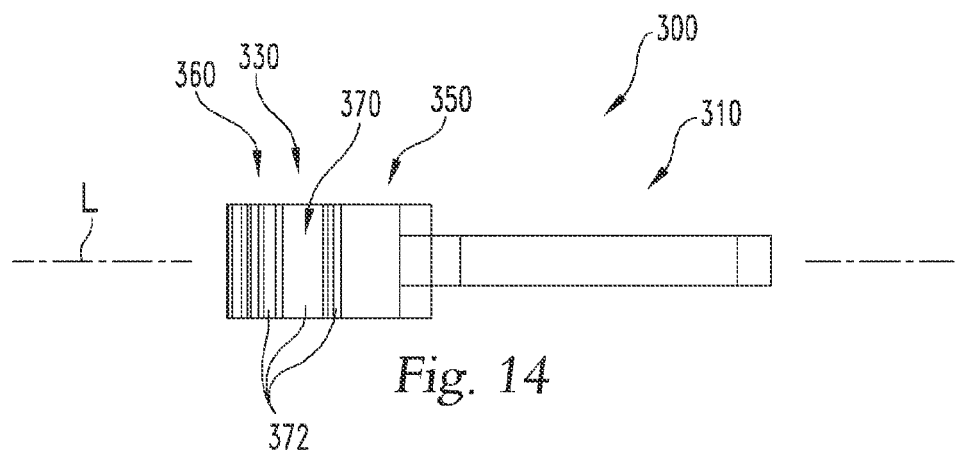
FIG. 14 is a plan view of the clamp element of FIG. 13.
Figure 15:
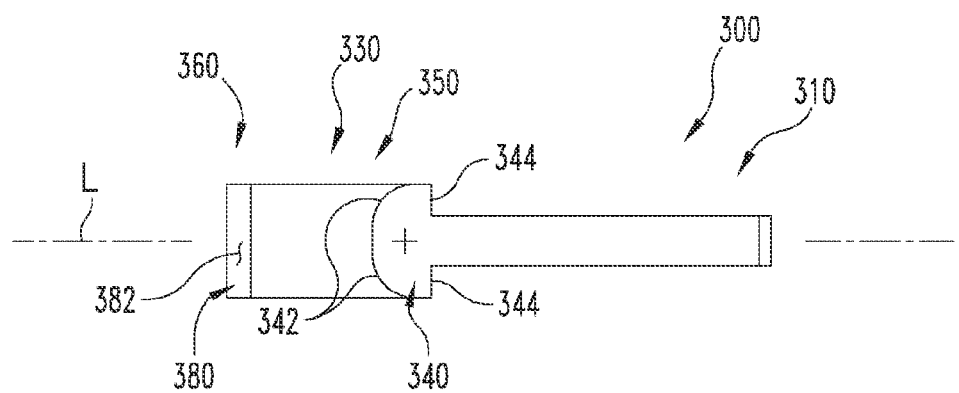
FIG. 15 is an opposite plan view of the clamp element of FIG. 13.

Referring to FIGS. 13-15, shown therein are further details regarding the clamp element 300. In the illustrated embodiment, the clamp element 300 extends along a longitudinal axis L and generally includes a proximal connection plate portion 310 and a distal clamp portion 330. The proximal connection plate portion 310 is configured for movable connection and slidable displacement within the gap 266 formed between the flanges 264a, 264b of the distal connection portion 260 of the compression element 200. The distal clamp portion 330 is configured for sliding engagement with the distal end portion 252 of the compression element 200, and is also configured for clamping or compressed engagement against the connection post 80 of the broach 60 to rigidly and releasably connect the broach 60 to the handle assembly 50.

In the illustrated embodiment, the proximal connection plate 310 of the clamp element 300 has a flat/planar plate-like configuration and defines a pair of slotted openings 312a, 312b that are axially offset from one another along the longitudinal axis L. The slotted openings 312a, 312b are sized and shaped to slidably receive the dowel pins 166a, 166b therein which are rigidly attached to the distal connection portion 260 of the compression element 200. In the illustrated embodiment, each of the slotted openings 312a, 312b includes a first slot portion 320 including opposite side surfaces 322a, 322b extending generally along the longitudinal axis L, and a second slot portion 324 extending from the first slot portion 320 at an angle and including opposite side surfaces 326a, 326b extending along an oblique axis O arranged at an oblique angle relative to the longitudinal axis L. In this manner, the obliquely-extending side surfaces 326a, 326b of the second slot portion 324 are ramped or angled relative to the longitudinal axis L. Additionally, the slot portions 320, 324 each define a slot width sized slightly larger than the outer diameter of the dowel pins 166a, 166b. As a result, displacement of the compression element 200 in a direction along the longitudinal axis L will slidably displace the dowel pins 166a, 166b generally along at least one of the slot portions 320, 324 of the slotted openings 312a, 312b, further details of which will be set forth below.

In the illustrated embodiment, the distal clamp 330 of the clamp element 300 includes a transverse base portion 340 attached to a distal end of the proximal connection plate 310, an axial plate portion 350 extending generally along the longitudinal axis L and oriented transverse to the base portion 340, and an enlarged clamp head portion 360 extending axially from the plate portion 350. The transverse base 340 has an overall width sized in relatively close tolerance with the inner width dimension of the hollow interior 132 of the axial handle 100 (as measured between the inner surfaces of the longitudinal side walls 110a, 110b) to properly position and/or guide the clamp element 300 within the hollow interior 132 of the axial handle 100. The distal corners 342 of the transverse base portion 340 may be rounded to facilitate sliding engagement with the inner surfaces of the axial handle 100. Additionally, the transverse base portion 340 defines a pair of proximally-facing surfaces or shoulders 344 positioned on opposite sides thereof that are engagable with distally-facing end surfaces 268 of the flanges 264a, 264b of the compression element 200 to properly position the distal end portion 252 of the compression element 200 relative to the clamp head 360 of the clamp element 300 when the handle assembly 50 is transitioned to a locked configuration. The plate portion 350 extends axially from the transverse base 340 and has a generally flat/planar configuration. However, other suitable configurations of the transverse base 340 and the axially plate 350 are also contemplated.

In the illustrated embodiment, the enlarged clamp head 360 has an irregular-shaped configuration defining a wedge or bearing surface 370 configured for sliding engagement with the distal end portion 252 of the compression element 200, and a clamp surface 380 configured for clamping/compressed engagement against the connection post 80 of the broach 60 to rigidly and releasably connect the broach 60 to the handle assembly 50. The wedge surface 370 is angled relative to the longitudinal axis L so as to define a ramp or incline. In the illustrated embodiment, the wedge surface 370 includes multiple ramped portions 372 that may define different incline angles. However, in other embodiments, the wedge surface 370 may define a single ramped portion defining a uniform or constant incline angle. In the illustrated embodiment, the ramped portions 372 are each generally flat/planar. However, other embodiments are also contemplated wherein one or more of the ramped portions 372 may be curved or may have a curvi-linear configuration. In the illustrated embodiment, the clamp surface 380 includes a first clamp surface 382 extending in an axial direction generally along the longitudinal axis L, and a second clamp surface 384 extending in a transverse direction substantially normal or perpendicular to the first clamp surface 382 so as to define a V-shaped projection or tongue 386 sized and shaped for receipt with the V-shaped notch 82 formed in the connection post 80 of the broach 60. The intersection or corner formed between the first and second clamp surfaces 382, 384 may be rounded or beveled. Additionally, in the illustrated embodiment, the clamp surfaces 382, 384 are each generally flat/planar. However, other embodiments are also contemplated wherein one or both of the clamp surfaces 382, 384 may be provided with a curved or curvi-linear configuration. Although a particular configuration of the clamp head 360 has been illustrated and described herein, other suitable configurations of the clamp head 360 are also contemplated.

Figure 16:
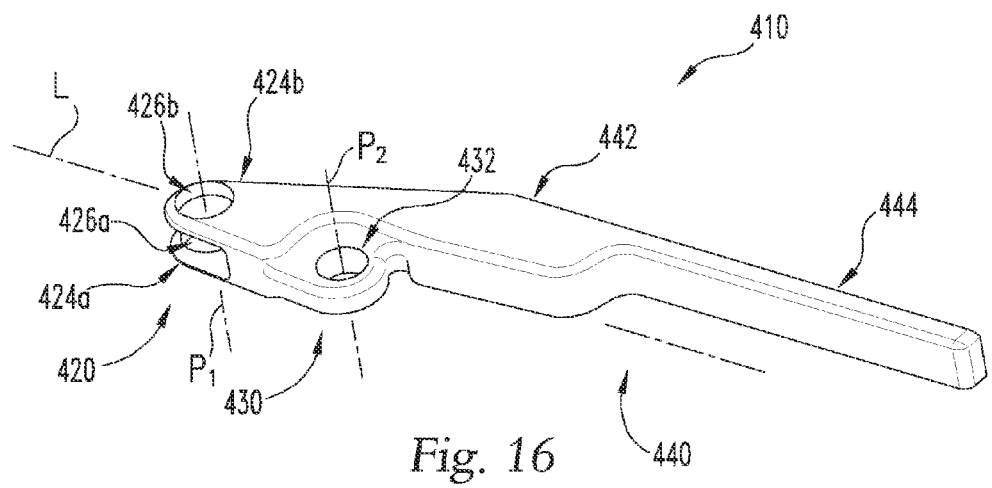
FIG. 16 is a perspective view of one embodiment of a toggle handle for use in association with the linkage assembly of FIG. 9.
Figure 17:
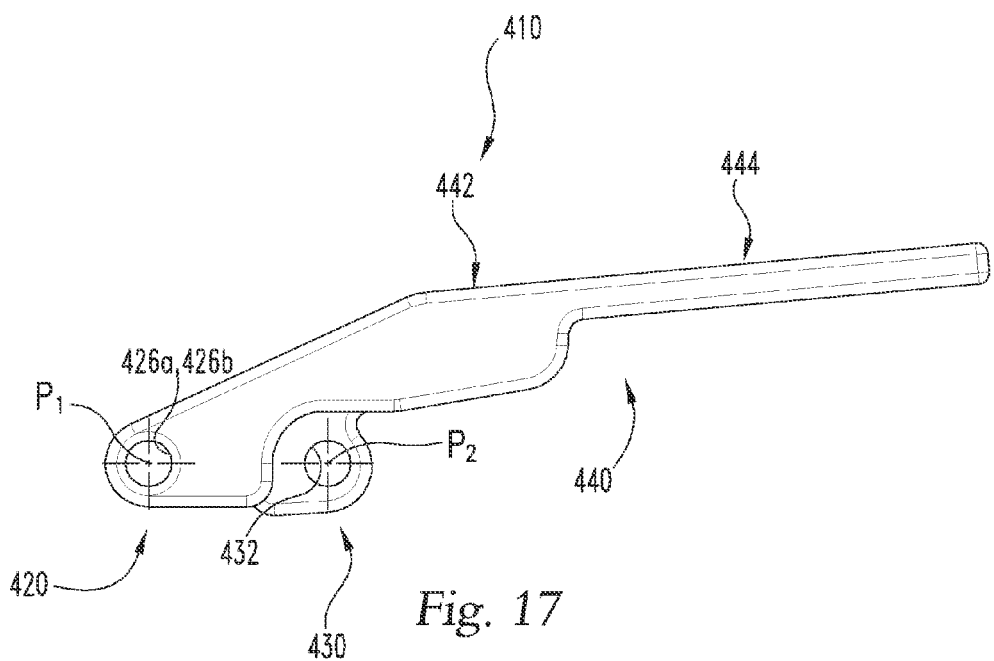
FIG. 17 is a side view of the toggle handle of FIG. 16.

Referring to FIGS. 16 and 17, shown therein are further details regarding the toggle handle or lever arm 410. In the illustrated embodiment, the toggle handle 410 includes a clevis portion 420 arranged at a distal end thereof and configured for pivotal connection with the proximal connection portion 210 of the compression element 200, a flange portion 430 proximally offset from clevis portion 420 and configured for pivotal connection with a distal portion of the toggle link 450, and an elongate lever portion 440 extending proximally from the flange portion 430 and configured to be grasped and manipulated by the surgeon.

In the illustrated embodiment, the clevis portion 420 of the toggle handle 410 includes a pair of spaced apart plates or flanges 424a, 424b defining a yoke or space therebetween sized to receive the proximal connection portion 210 of the compression element 200 therein, and with the plates 424a, 424b defining a pair of aligned openings 426a, 426b arranged along the first pivot axis $P_1$ and sized to receive the pivot pin 160 therein to pivotally connect the toggle handle 410 to the compression element 200 (FIG. 9). The flange portion 430 of the toggle handle 410 has a plate-like configuration and defines an opening 432 arranged along the second pivot axis $P_2$ and sized to receive the pivot pin 162 therein to pivotally connect the toggle handle 410 to a distal portion of the toggle link 450 (FIG. 9). The elongate lever portion 440 of the toggle handle 410 includes a base portion 442 and a proximal gripping portion 444 extending therefrom which is positioned adjacent the transverse recess 126 of the axial handle 100 (FIGS. 1 and 2) such that the proximal gripping portion 444 may be readily grasped and manipulated by one or more fingers and/or the thumb of the surgeon. Although a particular configuration of the toggle handle 410 has been illustrated and described herein, it should be understood that other suitable configurations are also contemplated.

Figure 18:
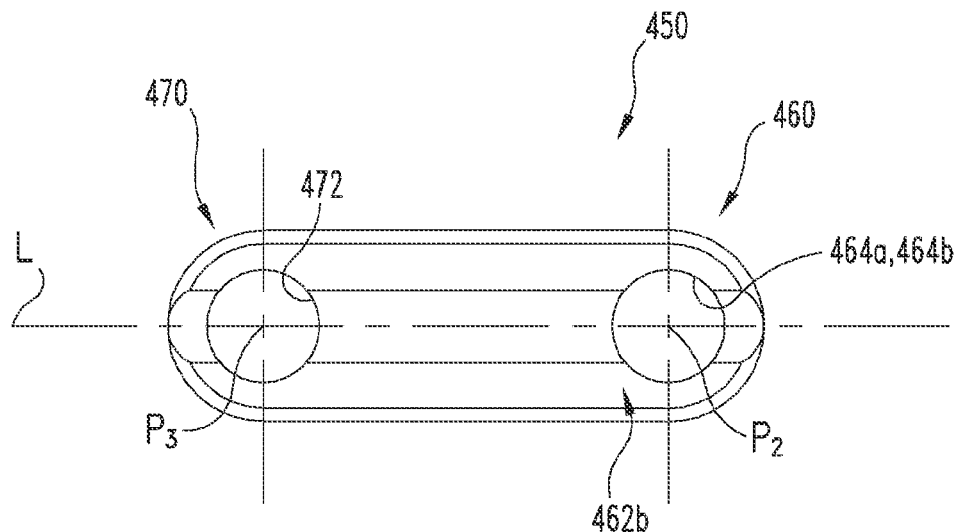
FIG. 18 is a side view of one embodiment of a toggle link for use in association with the linkage assembly of FIG. 9.
Figure 19:
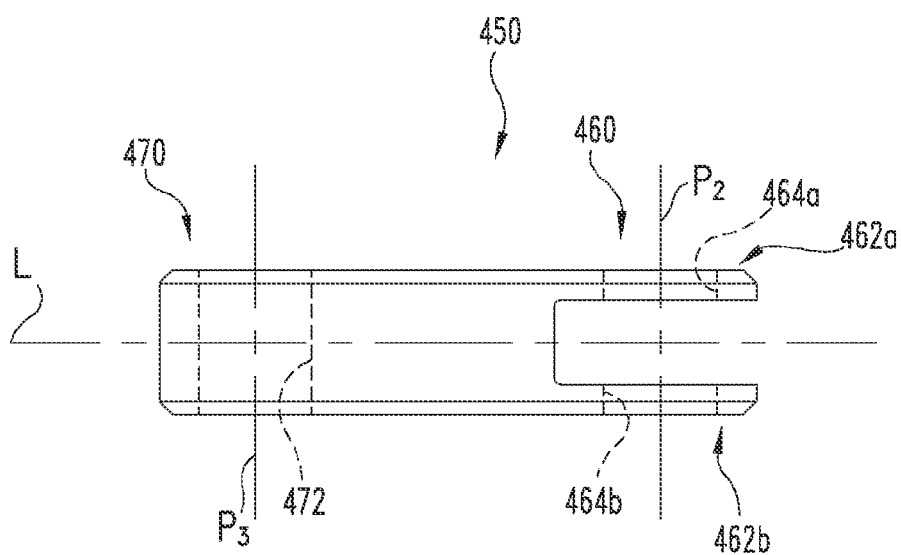
FIG. 19 is a plan view of the toggle link of FIG. 18.

Referring to FIGS. 18 and 19, shown therein are further details regarding the toggle link or pivot bar 450. In the illustrated embodiment, a distal end of the toggle link 450 includes a clevis portion 460 and the proximal end of the toggle link 450 includes a pivot connection portion 470. The clevis portion 460 includes a pair of spaced apart plates or flanges 462a, 462b defining a yoke or space therebetween sized to receive the flange portion 430 of the toggle handle 410 therein, and with the plates 462a, 462b defining a pair of aligned openings 464a, 464b arranged along the second pivot axis $P_2$ and sized to receive the pivot pin 162 therein to pivotally connect the toggle link 450 to the toggle handle 410 (FIG. 9). The pivot connection portion 470 of the toggle link 450 defines an opening 472 extending therethrough along the third pivot axis $P_3$ and sized to receive the pivot pin 164 therein to pivotally connect the toggle link 450 to the axial handle 100 (FIG. 9). Although a particular configuration of the toggle link 450 has been illustrated and described herein, it should be understood that other suitable configurations are also contemplated.

Referring once again to FIG. 9, pivotal movement of the toggle handle 410 about the pivot axis $P_1$ in an outward direction away from the longitudinal axis L correspondingly reduces the distance d between the pivot axes $P_1$ and $P_3$, which in turn pulls the compression element 200 and proximally displaces the compression element 200 in the direction of arrow A to transition the handle assembly 50 to an unlocked configuration that permits the broach 60 to be engaged with and/or released from the handle assembly 50 (FIG. 4A). Conversely, pivotal movement of the toggle handle 410 about the pivot axis $P_1$ in an inward direction toward the longitudinal axis L correspondingly increases the distance d between the pivot axes $P_1$ and $P_3$, which in turn pushes the compression element 200 and distally displaces the compression element 200 in the direction of arrow B to transition the handle assembly 50 to a locked configuration to rigidly engage the broach 60 to the handle assembly 50 (FIG. 4B). Although a toggle-type actuator mechanism 400 has been illustrated and described herein for use in association with the handle assembly 50, it should be understood that other suitable actuator mechanisms are also contemplated to axially displace the compression element 200 in the direction of arrow A/B to transition the handle assembly 50 between the locked and unlocked configurations. For example, in other embodiments, a cam actuator mechanism, a screw-type actuator mechanism, a worm/thread mechanism, a rack and pinion mechanism, a piston actuator mechanism, a ratchet actuator mechanism, an electrical actuator, a pneumatic actuator (including $CO_2$ cartridge-type actuators), a hydraulic actuator, or other suitable actuator mechanisms may be used in association with the handle 100 to transition the handle assembly 50 between the locked and unlocked configurations.

Having described the components, features and functional characteristics associated with the handle assembly 50, reference will now be made to engagement of the handle assembly 50 to the broach 60 according to one form of the present invention.

Referring initially to FIGS. 4 and 4A, the toggle handle 410 is initially pivoted about the pivot axis $P_1$ in an outward direction away from the longitudinal axis L, which in turn proximally displaces the compression element 200 in the direction of arrow A to transition the handle assembly 50 to the unlocked configuration illustrated in FIG. 4A. As the compression element 200 is displaced in the direction of arrow A, the dowel pins 166a, 166b attached to the distal connection plate portion 260 of the compression element 200 are movably displaced along the oblique slot portions 324 defined by the slotted openings 312a, 312b in the clamp element 300, which in turn displaces the clamp element 300 generally along the transverse axis T and away from the distal passage 138 of the axial shaft 100 to thereby retract the clamp head 360 away from the connection axis C and out of the distal passage 138 to permit insertion of the connection post 80 of the broach 60 into the distal passage 138. As indicated above, in one embodiment, movement of the clamp element 300 along the first and second vectors (i.e., along the longitudinal axis L and the transverse axis T) may occur simultaneously as a composite movement extending at an oblique angle relative to the longitudinal axis L and the transverse axis T.

Referring to FIGS. 4 and 4B, once the connection post 80 is properly positioned within the distal passage 138 and the broach 60 is rotated to the desired orientation about the connection axis C, the toggle handle 410 is pivoted about the pivot axis $P_1$ in an inward direction toward from the longitudinal axis L, which correspondingly distally displaces the compression element 200 in the direction of arrow B to transition the handle assembly 50 to the locked configuration illustrated in FIG. 4B. As the compression element 200 is displaced in the direction of arrow B, the distal end portion 252 of the compression element 200 is slidably engaged along the inclined/angled wedge surface 370 defined by the clamp head 360 of the clamp element 300. As should be appreciated, sliding engagement of the distal end portion 252 of the compression element 200 along the inclined/angled wedge surface 370 of the clamp head 360 correspondingly displaces the clamp element 300 along the longitudinal axis L and along the transverse axis T toward the connection post 80 of the broach 60. However, as indicated above, movement of the clamp element 300 may occur simultaneously along first and second vectors (i.e., along the longitudinal axis L and the transverse axis T) to provide a composite-type movement.

The V-shaped projection 386 defined by the clamp head 360 is driven into engagement with the V-shaped notch 84 of the connection post 80 until the clamp surfaces 382, 384 of the projection 386 are compressed firmly against the inner bearing surfaces of the V-shaped notch 84, which in turn compresses the connection post 80 against the opposite side wall of the distal passage 138 to thereby securely and rigidly connect the broach 60 to the handle assembly 50. Additionally, the overall strength and rigidity of the connection between the handle assembly 50 and the broach 60 is enhanced via the tight sandwiching/stacking of the distal end portion 252 of the compression element 200 between the clamp head 360 and the longitudinal wall 112b of the axial shaft 100. In this manner, the longitudinal wall 112b of the axial shaft 100 acts as a backstop or a buttress to prevent movement and/or deflection of the distal end portion 252 of the compression element 200 and the clamp head 360, thereby increasing the strength and rigidity of the connection between the handle assembly 50 and the broach 60.

As should be appreciated, the spring-like characteristics exhibited by the compression portion 220 (i.e., the flexible elasticity and resiliency) of the compression element 200 permits the application of a maximal axial force against the wedge surface 370 defined by the clamp head 360 regardless of potential tolerance gaps, dimensional variations, or misalignments between the components of the handle assembly 50, and/or potential tolerance gaps, dimensional variations, or misalignments between the handle assembly 50 (i.e., the clamp head 360 and the distal passage 138) and the connection post 80 of the broach 60. In this manner, the spring-like characteristics of the compression portion 220 in combination with the actuation force generated by the linkage assembly 150 provide the handle assembly 50 with a clamping action similar to that of a vice-grip tool to thereby provide a secure and rigid connection between the handle assembly 50 and the broach 60. As should also be appreciated, the secure and rigid connection between the broach 60 and the handle assembly 50 eliminates or at least minimizes motion (e.g., micro-motion) and/or deflection therebetween, thereby providing various advantages including, for example, increased control of the broach 60, increased visual and tactile feedback to the surgeon as to the fit of the broach 60 within the femoral canal, an increased ability of the surgeon to more precisely estimate the resulting tightness of fit of a femoral stem within the femoral canal, and/or easier removal of the broach 60 from the femoral canal subsequent to shaping.

Subsequent to use of the handle assembly 50 and the broach 60 to shape the femoral canal, the toggle handle 410 may once again be pivoted in an outward direction away from the longitudinal axis L to transition the handle assembly 50 back to the unlocked configuration illustrated in FIG. 4A, thereby releasing the clamping force exerted onto the connection post 80 to permit removal of the broach 60 from the handle assembly 50. As should be further appreciated, various types, configurations and/or sizes of orthopedic shaping/cutting members may be used interchangeably in association with the handle assembly 50, and a set or series of modular broaches or other shaping/cutting members may be provided as a kit along with the handle assembly 50.

Figure 20:
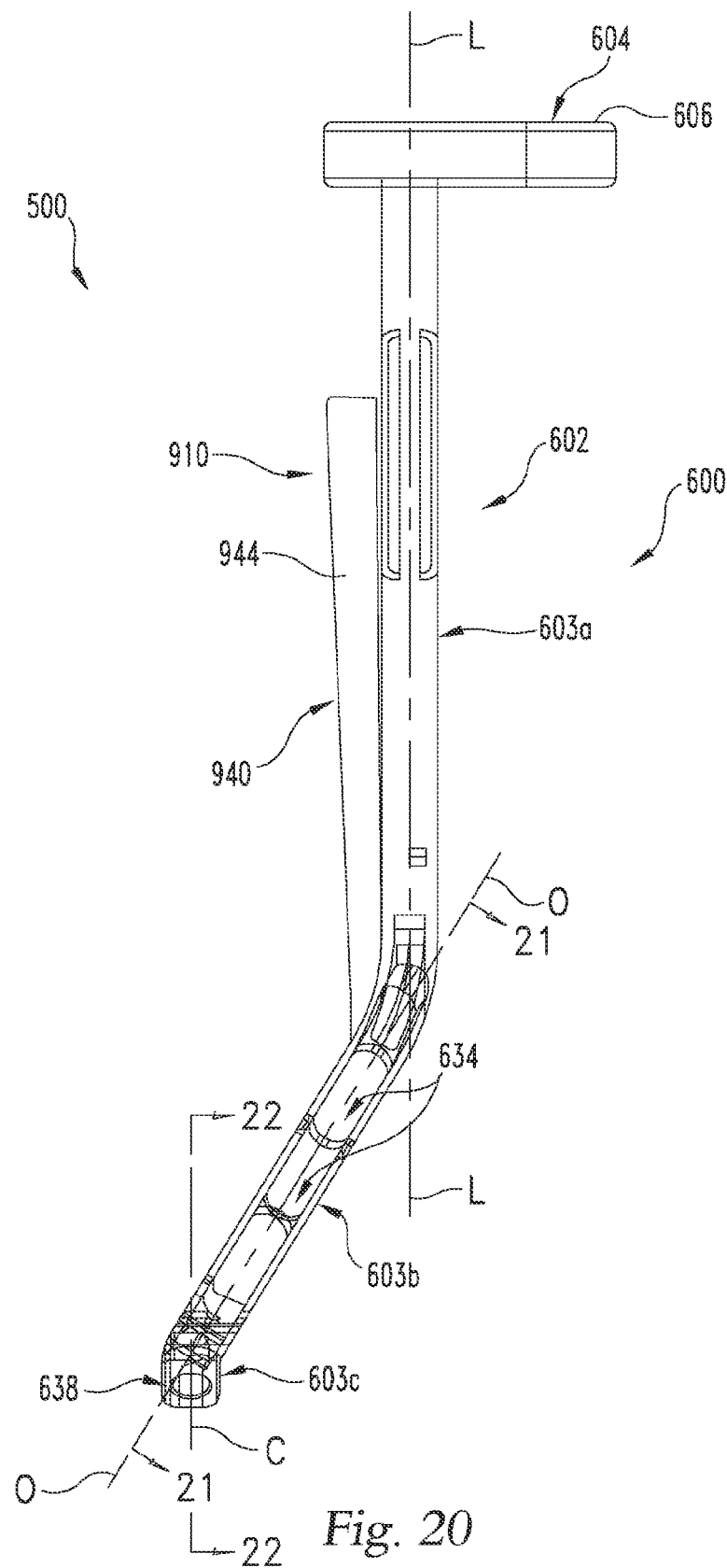
FIG. 20 is a side view of a surgical instrument handle assembly according to another form of the present invention.
Figure 21:
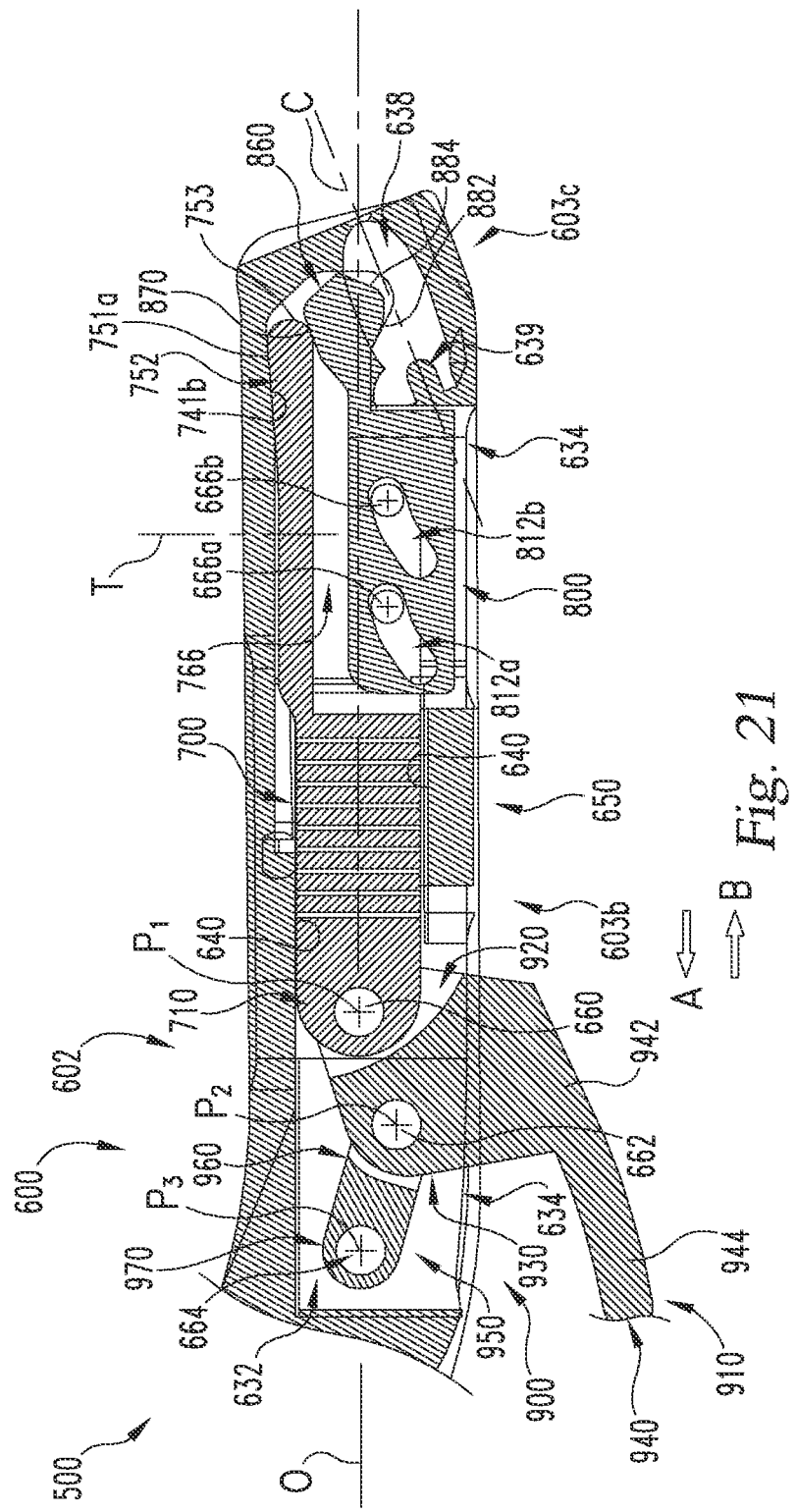
FIG. 21 is a cross-section of the surgical instrument handle assembly of FIG. 20, as taken along line 21-21 of FIG. 20.
Figure 22:
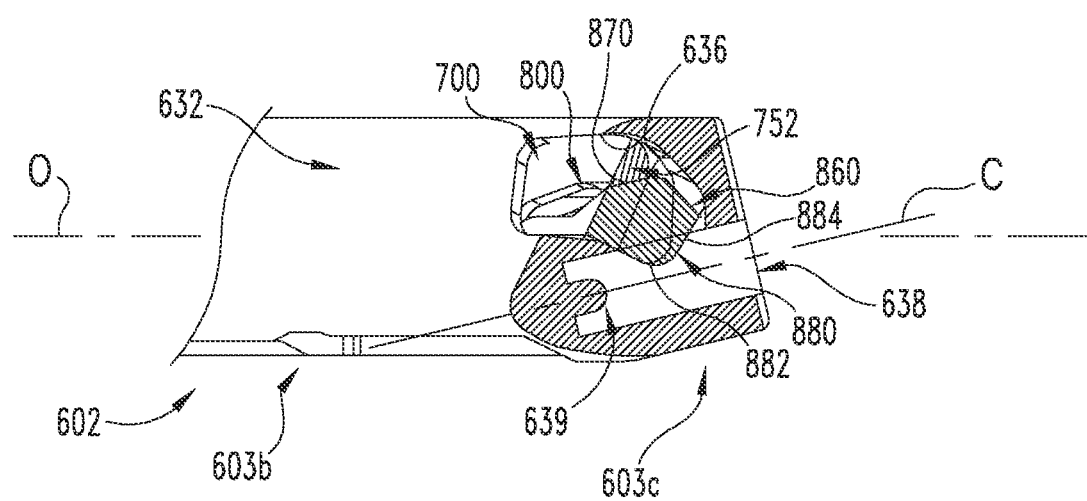
FIG. 22 is a cross-section of the surgical instrument handle assembly of FIG. 20, as taken along line 22-22 of FIG. 20.

Referring to FIGS. 20-22, shown therein is a surgical instrument handle assembly 500 according to another form of the invention that is configured for preparation of the intramedullary canal of a femur in a total hip replacement surgery or other orthopedic surgeries. The handle assembly 500 has many of the same components and features as the handle assembly 50 illustrated and described above, and is similarly configured for rigid and releasable connection to an orthopedic device such as, for example, the broach 60 illustrated and described above (FIGS. 4A and 4B). In addition to the broach 60, the handle assembly 500 may also be used in association with other configurations of broaches, other types and configurations of shaping/cutting members, other orthopedic devices, or orthopedic implants. However, unlike the handle assembly 50 which is provided with an axial handle 100 having a generally linear elongate shaft 102 extending along a single longitudinal axis L, the illustrated embodiment of the handle assembly 500 is provided with a handle 600 including an elongate shaft 602 having an axial shaft portion 603a, an offset shaft portion 603b, and a distal transition portion 603c.

Similar to the handle assembly 50 illustrated and described above, the handle assembly 500 is likewise provided with a linkage assembly 650 (FIG. 21) movably connected to the handle 600, and similarly includes a compression element 700, a clamp element 800, and an actuator mechanism 900. In the illustrated embodiment, the actuator mechanism 900 is a toggle-type actuator and generally includes a toggle handle 910 and a toggle link 950. As should be appreciated, the linkage assembly 650 of the handle assembly 500 (i.e., the compression element 700, the clamp element 800, and the actuator mechanism 900) is similar in structure and function to the linkage assembly 150 of the handle assembly 50 (i.e., the compression element 200, the clamp element 300, and the actuator mechanism 400) illustrated and described above. The handle assembly 500 likewise operates in a manner similar to that of the handle assembly 50 to provide a secure and rigid connection with the shaping member 60. However, structural differences between certain components of the handle assembly 500 and corresponding components of the handle assembly 50 may be apparent. Some of these structural differences are illustrated in FIGS. 20-30 in association with the following description.

As indicated above, the illustrated embodiment of the handle 600 includes an axial shaft portion 603a, an offset shaft portion 603b, and a distal transition portion 603c. The axial shaft portion 603a has a linear configuration arranged generally along a longitudinal axis L. The offset shaft portion 603b extends from the axial shaft portion 603a and is arranged generally along an offset axis O that defines one or more angular offsets relative to the longitudinal axis L. In the illustrated embodiment, the offset axis O of the offset shaft portion 603b defines both an anterior offset and a lateral offset relative to the longitudinal axis L. However, other embodiments are also contemplated where the offset shaft portion 603b is arranged such that the offset axis O defines a single offset or other types of compound offsets relative to the longitudinal axis L. As should be appreciated, providing the elongate shaft 602 with one or more angular offsets (via inclusion of the offset shaft portion 603b) may be beneficial when inserting the shaping member 60 into the femoral intramedullary canal using an anterior surgical approach to minimize interference with adjacent soft tissues or other anatomic structures surrounding the hip joint of the patient. The distal transition portion 603c extends from the offset shaft portion 603b and defines a distal post-receiving passage 638 (similar to the distal post-receiving passage 138 defined by the axial shaft 100 of the handle assembly 50) sized and shaped for receipt of the connection post 80 of the broach 60.

The distal post-receiving passage 638 is arranged along a connection axis C oriented at an oblique angle relative to the offset axis O. However, other embodiments are also contemplated wherein the elongate shaft 602 does not include a distal transition portion 603c, with the distal post-receiving passage 638 defined by a distal region of the offset shaft portion 603b. In the illustrated embodiment, the connection axis C is arranged generally parallel with the longitudinal axis L of the axial shaft portion 603a, albeit offset from the longitudinal axis L in one or more directions (e.g., in anterior and lateral directions). However, other embodiments are also contemplated where the connection axis C may be angled relative to the longitudinal axis L of the axial shaft portion 603a. Additionally, as shown in FIG. 22, the handle shaft 602 defines a projection 639 extending into the post-receiving passage 638 and arranged generally along the connection axis C. The projection 639 is sized and shaped for receipt within the axial notch or groove 86 formed in the end of the connection post 80 of the broach 60 (FIG. 4A). In the illustrated embodiment, the projection 639 and the axial notch 86 each have a semi-circular configuration. However, other suitable shapes and configurations are also contemplated. Receipt of the projection 639 within the axial notch 86 in the broach connection post 80 provides an added degree of strength and rigidity to the connection of the broach 60 to the handle assembly 500. As should be appreciated, the shape, configuration, position and/or geometry of the post-receiving passage 638 may be varied to accommodate/control various aspects associated with the handle assembly 500 and its relation relative to the broach 60 (i.e., the orientation/position of the broach 60 relative to one or more portions of the handle assembly 500).

In the illustrated embodiment, the handle 600 includes a strike plate or impaction platform 604 similar in structure and function to the impaction platform 104 illustrated and described above. The impaction platform 604 has a generally flat/planar proximally-facing impact or strike surface 606 and is operatively attached to a proximal end portion of the axial shaft portion 603a. However, other shapes and configurations of the impaction platform 604 are also contemplated. As should be appreciated, the shape, configuration, position, orientation and/or geometry of the impaction platform 604 including the particular shape, configuration, position, orientation and/or geometry of the impact or strike surface 606 may be varied to accommodate/control various aspects associated with the handle assembly 500 and its relation to the broach 60.

In the illustrated embodiment, the axial shaft portion 603a, the offset shaft portion 603b, and the distal transition portion 603c each have a generally linear configuration and each define a generally rectangular outer transverse cross-section. However, other shapes and configurations are also contemplated. At least the offset shaft portion 603b and the distal transition portion 603c define a hollow interior or inner chamber 632 to house the components of the linkage assembly 650. The offset shaft portion 603b may be provided with a number of slotted openings 634 extending transversely through one or more shaft walls and into communication with the hollow interior 632. The offset shaft portion 603b and/or the distal transition portion 603c may also define a window 636 (FIG. 22) extending transversely therethrough and into communication with the hollow interior 632. The slotted openings 634 and the window 636 provide ready access to the components contained within the hollow interior 632, aid in manufacturing, assembly and/or maintenance of the handle assembly 500, facilitate cleaning and/or sterilization of the handle assembly 500, and/or may provide direct visualization of the components contained within the hollow interior 632 to verify proper operation. Additionally, as indicated above, the distal transition portion 603c of the shaft 602 defines a distal post-receiving passage 638 arranged along the connection axis C and extending through a distal end wall and into communication with the hollow interior 632.

In the illustrated embodiment, the offset shaft portion 603b is also provided with a number of raised lands or plateaus 640 extending inwardly into the hollow interior 632 and defining generally flat/planar bearing surfaces configured to guide the compression element 700 and/or the clamp element 800 in a direction generally parallel with the offset axis O upon actuation of the actuator mechanism 900. It should be understood that other features or structures may also be provided to further aid in guiding the compression element 700 and/or the clamp element 800 in a direction generally along the offset axis O and/or to add strength and structural integrity to the linkage assembly 650. For example, one or more guide pins may be positioned at locations along the hollowing interior 632 to further aid in guiding the compression element 700 and/or the clamp element 800 upon actuation of the actuator mechanism 900.

Referring specifically to FIG. 21, the linkage assembly 650 generally includes a compression element 700, a clamp element 800, and an actuator mechanism 900 comprised of a toggle handle 910 and a toggle link 950. In the illustrated embodiment, the components of the linkage assembly 650 are interconnected via a series of pins or shafts. Specifically, a proximal portion of the compression element 700 is pivotally connected to a first portion of the toggle handle 910 via a first pivot pin 660 extending along a first pivot axis $P_1$ to permit pivotal movement of the toggle handle 910 relative to the compression element 700 about the first pivot axis $P_1$. A second portion of the toggle handle 910 is pivotally connected to a distal portion of the toggle link 950 via a second pivot pin 662 extending along a second pivot axis $P_2$ to permit pivotal movement of the toggle handle 910 relative to the toggle link 950 about the second pivot axis $P_2$. Additionally, a proximal portion of the toggle link 950 is pivotally connected to the offset shaft portion 603*b* of the shaft 602 via a third pivot pin 664 extending along a third pivot axis $P_3$ to permit pivotal movement of the toggle link 950 relative to the handle 600 about the third pivot axis $P_3$ while preventing axially displacement of the toggle link 950 along the offset axis O.

Furthermore, a distal portion of the compression element 700 is slidably attached to the clamp element 800 via a pair of dowel pins 666*a*, 666*b* to permit a degree of relative axial movement of the compression element 700 relative to the clamp element 800 along a first vector arranged generally parallel with the offset axis O, as well as a degree of relative transverse movement of the clamp element 700 relative to the compression element 800 generally along a second vector arranged generally parallel with a transverse axis T oriented substantially normal to the offset axis O, further details of which will be set forth below. It should be appreciated that in one embodiment, movement of the compression element 700 relative to the clamp element 800 along the first and second vectors may occur simultaneously as a composite movement extending at an oblique angle relative to the offset axis O and the transverse axis T. However, other embodiments and other types of movement between the compression element 700 and the clamp element 800 are also contemplated, including sequential movement of the clamp element 800 along the first and second vectors or directions of travel.

As should be appreciated, the linkage assembly 650 operates in a manner similar to the linkage assembly 150 illustrated and described above. Specifically, pivotal movement of the toggle handle 910 about the pivot axis $P_1$ in an outward direction away from the offset axis O correspondingly pivots the toggle link 950 about the pivot axis $P_3$ in an outward direction away from the offset axis O. This outward pivotal movement of the toggle handle 910 and the toggle link 950 reduces the distance between the pivot axes $P_1$ and $P_3$. Since the proximal portion of the toggle link 950 remains in a stationary axial position (via the pivot pin 664 attached to the handle shaft 602), outward pivotal movement of the toggle handle 910 and the toggle link 950 pulls the compression element 700 in a proximal direction, which in turn proximally displaces the compression element 700 in the direction of arrow A generally along the offset axis O. Conversely, pivotal movement of the toggle handle 910 about the pivot axis $P_1$ in an inward direction toward the offset axis O correspondingly pivots the toggle link 950 about the pivot axis $P_3$ in an inward direction toward the offset axis O. This inward pivotal movement of the toggle handle 910 and the toggle link 950 increases the distance between the pivot axes $P_1$ and $P_3$ and pushes the compression element 700 in a distal direction, which in turn distally displaces the compression element 700 in the direction of arrow B generally along the offset axis O. As should be appreciated, the proximal/distal movement of the compression element 700 in the direction of arrows A/B serves to transition the compression element 700 and the clamp element 800 between unlocked and locked configurations. Although a toggle-type actuator mechanism 900 has been illustrated and described herein for use in association with the handle assembly 500, it should be understood that other suitable actuator mechanisms are also contemplated to axially displace the compression element 700 in the direction of arrow A/B. For example, in other embodiments, a cam actuator mechanism, a screw-type actuator mechanism, a worm/thread mechanism, a rack and pinion mechanism, a piston actuator mechanism, a ratchet actuator mechanism, an electrical actuator, a pneumatic actuator (including $CO_2$ cartridge-type actuators), a hydraulic actuator, or other suitable actuator mechanisms may be used in association with the handle 600 to transition the handle assembly 500 between the locked and unlocked configurations.

Referring to FIGS. 23-25, shown therein are further details regarding the compression element 700. In the illustrated embodiment, the compression element 700 has a rod or shaft-like configuration extending along a longitudinal axis L. Additionally, the compression element 700 generally includes a proximal connection portion or pivot plate member 710 configured for pivotal connection with the toggle handle 910, a compression portion or spring-like member 720 having spring-like characteristics exhibiting flexibly elastic resiliency along the longitudinal axis L, and a distal engagement portion or pusher member 740 configured for movable/slidable engagement with the clamp element 800 to force the clamp element 800 into compressed engagement against the connection post 80 of the broach 60 to thereby rigidly and releasably connect the broach 60 to the handle assembly 500. In the illustrated embodiment, the proximal connection portion 710, the compression portion 720, and the distal engagement portion 740 are integral with one another to provide the compression element 700 as a single-piece monolithic structure. However, in other embodiments, one or more portions of the compression element 700 may be provided as separate members that are assembled together to form a multi-piece compression element 700.

In the illustrated embodiment, the proximal connection portion or pivot plate member 710 of the compression element 700 has a plate-like configuration defining an opening 712 extending therethrough in a direction transverse to the longitudinal axis L. The opening 712 is positioned along the pivot axis $P_1$ and is sized to receive the pivot pin 660 therein to pivotally connect the compression element 700 to the toggle handle 910 (FIG. 21). Although a particular configuration of the proximal connection portion 710 has been illustrated and described herein, it should be understood that other suitable configurations are also contemplated.

In the illustrated embodiment, the compression portion or spring member 720 of the compression element 700 has a substantially rectangular outer transverse cross-section including opposite first and second longitudinal sides 722a, 722b defining an overall width dimension w therebetween, and opposite first and second longitudinal edges 724a, 724b defining an overall height dimension h therebetween. As indicated above, the compression portion 720 has spring-like characteristics exhibiting flexibly elastic resiliency along the longitudinal axis L. The spring-like characteristics are provided by a first series of slots or slits 730a extending from the first longitudinal side 722a and transversely across a portion of the overall width dimension w and along the entire overall height dimension h, and a second series of slots or slits 730b extending from the second longitudinal side 722b and transversely across a portion of the overall width dimension w and along the entire overall height dimension h. In the illustrated embodiment, the slits 730a, 730b are offset from one another along the length of the compression portion 720 in an alternating manner so as to define a relatively narrow strip of material 732 extending along the longitudinal axis L in an undulating or sinusoidal configuration. In one embodiment, the slits 730a, 730b extend across greater than one-half of the overall width dimension w, and in a further embodiment extend across approximately three-quarters of the overall width dimension w. However, other embodiments are also contemplated where the slits 730a, 730b extend across other portions of the overall width dimension w. Additionally, in the illustrated embodiment, the slits 730a, 730b each have a uniform slit width. However, in other embodiments, the slits 730a, 730b may be provided with a non-uniform or varying slit width including, for example, an enlarged portion at the inner end of the slits 730a, 730b to provide additional flexibility and elasticity to the compression portion 720. As should be appreciated, the slits 730a, 730b provide the compression portion 720 with spring-like characteristics including flexibly elastic resiliency along the longitudinal axis L and to a lesser degree in directions transverse to the longitudinal axis L. Although a particular configuration of the compression portion 720 has been illustrated and described herein, it should be understood that other suitable spring-like configurations are also contemplated.

In the illustrated embodiment, the distal engagement portion or pusher member 740 of the compression element 700 generally includes an engagement plate portion 750 extending along the longitudinal axis L, and a connection portion 760 extending substantially perpendicularly from the engagement plate portion 750.

The engagement plate portion 750 defines a distal end portion 752 defining a distal engagement surface 754. In one embodiment, the distal engagement surface 754 has a curved or semi-circular configuration. However, other suitable shapes and configurations of the distal engagement surface 754 are also contemplated. Additionally, in the illustrated embodiment, the engagement plate portion 750 defines a first outer surface portion 751a arranged generally parallel with the longitudinal axis L, and a second outer surface portion 751b extending from the first outer surface portion 751a and defining a relatively small outward taper or incline extending toward and intersecting the engagement surface 754 of the distal end portion 752. The tapered outer surface portion 751b is engagable with a corresponding angled/undercut surface portion 741b formed along the distal end of the elongate shaft 602 (FIG. 21) when the linkage assembly 650 is positioned in a fully extended or locked state. Such engagement provides for rigid and secure engagement between the compression element 700 and the elongate shaft 602 and between the compression element 700 and the clamp element 800 when the handle assembly 500 is positioned in the fully extended/locked state (FIG. 21) to substantially prevent motion therebetween, which in turn provides for rigid and secure locked engagement between the handle assembly 500 and the connection post 80 of the broach 60.

In the illustrated embodiment, the connection portion 760 is configured as a U-shaped clevis including a pair of plates or flanges 764a, 764b extending transversely from the engagement plate portion 750 and spaced apart from one another to define a yoke or gap 766 therebetween sized for receipt of a portion of the clamping element 800 therein. The flanges 764a, 764b in turn define a pair of generally circular openings 762a, 762b that are axially offset from one another along the longitudinal axis L. The pair of openings 762a, 762b are sized and shaped to receive the dowel pins 666a, 666b therein, respectively, which are in turn positioned within corresponding slotted openings in the clamp element 800 to thereby movably and slidably connect the compression element 700 with the clamp element 800 with a portion of the clamp element 800 being guidingly displaced within the gap 766 between the flanges 764a, 764b. Positioning of a portion of the clamp element 800 within the gap 766 between the flanges 764a, 764b of the compression element 700 also serves to increase the strength and structural integrity of the slidable interconnection between the compression element 700 and the clamp element 800. Although a particular configuration of the distal engagement portion 740 has been illustrated and described herein, it should be understood that other suitable configurations are also contemplated.

Referring to FIGS. 26-30, shown therein are further details regarding the clamp element 800. In the illustrated embodiment, the clamp element 800 extends along a longitudinal axis L and generally includes a proximal connection plate portion 810 and a distal clamp portion 830. The proximal connection plate portion 810 is configured for movable connection and slidable displacement within the gap 766 formed between the flanges 764a, 764b of the distal connection portion 760 of the compression element 700. The distal clamp portion 830 is configured for sliding engagement with the distal end portion 752 of the compression element 700, and is also configured for clamping or compressed engagement against the connection post 80 of the broach 60 to rigidly and releasably connect the broach 60 to the handle assembly 500.

In the illustrated embodiment, the proximal connection plate 810 of the clamp element 800 has a flat/planar plate-like configuration and defines a pair of slotted openings 812a, 812b that are axially offset from one another along the longitudinal axis L. The slotted openings 812a, 812b are sized and shaped to slidably receive the dowel pins 666a, 666b which are rigidly attached to the distal connection plate 760 of the compression element 700. In the illustrated embodiment, each of the slotted openings 812a, 812b includes a first slot portion 820 including opposite side surfaces 822a, 822b extending generally along a first oblique axis $O_1$ arranged at an oblique angle relative to the longitudinal axis L, and a second slot portion 824 extending from the first slot portion 820 and including opposite side surfaces 826a, 826b extending along a second oblique axis $O_2$ arranged at an oblique angle relative to the first oblique axis $O_1$ and the longitudinal axis L. In this manner, the obliquely-extending side surfaces of the first and second slot portions 820, 824 are ramped or angled relative to the longitudinal axis L. Additionally, the slot portions 820, 824 each define a slot width sized slightly larger than the outer diameter of the dowel pins 666a, 666b. As a result, displacement of the compression element 700 in a direction along the longitudinal axis L will slidably displace the dowel pins 666a, 666b generally along at least one of the slot portions 820, 824 of the slotted openings 812a, 812b, further details of which will be set forth below. As indicated above, in one embodiment, movement of the clamp element 800 occurs along first and second vectors (i.e., along the offset axis O and the transverse axis T), which may occur simultaneously as a composite movement extending at an oblique angle relative to the offset axis O and the transverse axis T.

In the illustrated embodiment, the distal clamp 830 of the clamp element 800 includes a transverse base portion 840 attached to a distal end of the proximal connection plate 810, an axial plate portion 850 extending generally along the longitudinal axis L and oriented transverse to the base portion 840, and an enlarged clamp head portion 860 extending axially from the plate portion 850. The transverse base 840 has an overall width sized in relatively close tolerance with the inner width dimension of the hollow interior 632 of the handle 600 to properly position and/or guide the clamp element 800 within the hollow interior 632 of the handle 600. The distal corners 842 of the transverse base portion 840 may be rounded to facilitate sliding engagement with the inner surfaces of the handle 600. Additionally, the transverse base portion 840 defines a pair of proximally-facing surfaces or shoulders 844 positioned on opposite sides thereof that are engagable with distally-facing end surfaces 768 of the flanges 764a, 764b of the compression element 700 to properly position the distal end portion 752 of the compression element 700 relative to the clamp head 860 of the clamp element 800 when the handle assembly 500 is transitioned to a locked configuration. The plate portion 850 extends axially from the transverse base 840 and has a generally flat/planar configuration. However, other suitable configurations of the transverse base 840 and the axially plate 850 are also contemplated.

In the illustrated embodiment, the enlarged clamp head 860 has an irregular-shaped configuration defining a wedge or bearing surface 870 configured for sliding engagement with the distal end portion 752 of the compression element 700, and a clamp surface 880 configured for clamping/compressed engagement against the connection post 80 of the broach 60 to rigidly and releasably connect the broach 60 to the handle assembly 500. The wedge surface 870 is angled relative to the longitudinal axis L so as to define a ramp or incline. In the illustrated embodiment, the wedge surface 870 includes multiple ramped portions 872 that may define different incline angles. However, in other embodiments, the wedge surface 870 may define a single ramped portion defining a uniform or constant incline angle. In the illustrated embodiment, the ramped portions 872 are each generally flat/planar. However, other embodiments are also contemplated wherein one or more of the ramped portions 872 may be curved or may have a curvi-linear configuration. In the illustrated embodiment, the clamp surface 880 includes first and second clamp surfaces 882, 884 that together define a generally V-shaped projection or tongue 886 sized and shaped for receipt with the V-shaped notch 82 formed in the connection post 80 of the broach 60. The intersection or corner formed between the first and second clamp surfaces 882, 884 may be rounded or beveled. Additionally, in the illustrated embodiment, the clamp surfaces 882, 884 are each generally flat/planar. However, other embodiments are also contemplated wherein one or both of the clamp surfaces 882, 884 may be provided with a curved or curvi-linear configuration. Further, in the illustrated embodiment, the clamp surfaces 882, 884 extend along planes that are oblique (i.e., non-perpendicular and non-parallel) relative to central longitudinal planes P of the clamp element 800 (FIG. 29). In other words, the planes along which the clamp surfaces 382, 384 extend are skewed relative to central longitudinal planes P of the clamp element 800. Although a particular configuration of the clamp head 860 has been illustrated and described herein, other suitable configurations of the clamp head 860 are also contemplated. As should be appreciated, the geometry of the clamp head 860 including the particular shape and configuration of the clamp surfaces 882, 884 may be varied to accommodate/control various aspects associated with the handle assembly 500 and its relation relative to the broach 60 (i.e., the orientation/position of the broach 60 relative to one or more portions of the handle assembly 500).

Referring once again to FIGS. 20 and 21, in the illustrated embodiment, the toggle handle 910 includes a clevis portion 920 arranged at a distal end thereof and configured for pivotal connection with the proximal connection portion 710 of the compression element 700, a flange portion 930 proximally offset from clevis portion 920 and configured for pivotal connection with a distal portion of the toggle link 950, and an elongate lever portion 940 extending proximally from the flange portion 930 and configured to be grasped and manipulated by the surgeon. The clevis portion 920 includes a pair of spaced apart plates or flanges defining a yoke or space therebetween sized to receive the proximal connection portion 710 of the compression element 700 therein, and with the plates defining aligned openings arranged along the first pivot axis $P_1$ and sized to receive the pivot pin 660 therein to pivotally connect the toggle handle 910 to the compression element 700. The flange portion 930 has a plate-like configuration and defines an opening arranged along the second pivot axis $P_2$ and sized to receive the pivot pin 662 therein to pivotally connect the toggle handle 910 to a distal portion of the toggle link 950. The elongate lever portion 940 of the toggle handle 910 includes a base portion 942 and a proximal gripping portion 944 extending therefrom and positioned adjacent the axial shaft portion 603a of the handle 600 for grasping and manipulation by the surgeon. Although a particular configuration of the toggle handle 910 has been illustrated and described herein, it should be understood that other suitable configurations are also contemplated.

In the illustrated embodiment, the toggle link 950 includes a distal clevis portion 960 and a proximal pivot connection portion 970. The clevis portion 960 includes a pair of spaced apart plates or flanges defining a yoke or space therebetween sized to receive the flange portion 940 of the toggle handle 910 therein, and with the plates defining a pair of aligned openings arranged along the second pivot axis $P_2$ and sized to receive the pivot pin 662 therein to pivotally connect the toggle link 950 to the toggle handle 910. The pivot connection portion 970 defines an opening extending therethrough along the third pivot axis $P_3$ and sized to receive the pivot pin 664 therein to pivotally connect the toggle link 950 to the offset shaft portion 603b of the handle 600. Although a particular configuration of the toggle link 950 has been illustrated and described herein, it should be understood that other suitable configurations are also contemplated.

Having described the components, features and functional characteristics associated with the handle assembly 500, reference will now be made to engagement of the handle assembly 500 to the broach 60 according to one form of the present invention. Referring once again to FIGS. 20-22, the toggle handle 910 is initially pivoted about the pivot axis $P_1$ in an outward direction away from the offset axis O, which in turn pulls the compression element 700 and proximally displaces the compression element 700 in the direction of arrow A to transition the handle assembly 50 to an unlocked configuration. As the compression element 700 is displaced in the direction of arrow A, the dowel pins 666a, 666b attached to the distal connection plate portion 760 of the compression element 700 are movably displaced along one of the oblique slot portions 822, 824 defined by the slotted openings 812a, 812b in the clamp element 800, which in turn displaces the clamp element 800 in a transverse direction away from the distal passage 638 of the shaft 600 to thereby retract the clamp head 860 away from the connection axis C and out of the distal passage 638 to permit insertion of the connection post 80 of the broach 60 into the distal post-receiving passage 638. As indicated above, when the connection post 80 of the broach 60 is inserted into the distal post-receiving passage 638, the projection 639 (FIG. 22) is positioned within the axial notch 86 formed in the end of the connection post 80 (FIG. 4A) to provide an added degree of strength and rigidity to the connection of the broach 60 to the handle assembly 500.

Once the connection post 80 is properly positioned within the distal passage 638 and the broach 60 is rotated to the desired orientation about the connection axis C, the toggle handle 910 is pivoted about the pivot axis $P_1$ in an inward direction toward from the offset axis O, which correspondingly pushes the compression element 700 and distally displaces the compression element 700 in the direction of arrow B to transition the handle assembly 500 to a locked configuration. As the compression element 700 is displaced in the direction of arrow B, the distal end portion 752 of the compression element 700 is slidably engaged along the inclined/angled wedge surface 870 defined by the clamp head 860 of the clamp element 800. As should be appreciated, sliding engagement of the distal end portion 752 of the compression element 700 along the inclined/angled wedge surface 870 of the clamp head 360 correspondingly displaces the clamp element 800 in a direction transverse to the connection axis C toward the connection post 80 of the broach 60. As indicated above, movement of the clamp element 800 may occur simultaneously along first and second vectors (i.e., along the offset axis O and the transverse axis T) to provide a composite-type movement.

The V-shaped projection 886 defined by the clamp head 860 is driven into engagement with the V-shaped notch 84 of the connection post 80 until the clamp surfaces 882, 884 of the projection 886 are compressed firmly against the inner bearing surfaces of the V-shaped notch 84, which in turn compresses the connection post 80 against the opposite side wall of the distal passage 638 to thereby securely and rigidly connect the broach 60 to the handle assembly 500. Additionally, the overall strength and rigidity of the connection between the handle assembly 500 and the broach 60 is enhanced via the tight sandwiching/stacking of the distal end portion 752 of the compression element 700 between the clamp head 860 and an inner wall of the of the offset shaft portion 603b. In this manner, the inner wall of the of the offset shaft portion 603b acts as a backstop or a buttress to prevent movement and/or deflection of the distal end portion 752 of the compression element 700 and the clamp head 860, thereby increasing the strength and rigidity of the connection between the handle assembly 500 and the broach 60.

As should be appreciated, the spring-like characteristics exhibited by the compression portion 720 (i.e., the flexible elasticity and resiliency) of the compression element 700 permits the application of a maximal axial force against the wedge surface 870 defined by the clamp head 860 regardless of potential tolerance gaps, dimensional variations, or misalignments between the components of the handle assembly 500, and/or potential tolerance gaps, dimensional variations, or misalignments between the handle assembly 500 (i.e., the clamp head 860 and the distal passage 638) and the connection post 80 of the broach 60. In this manner, the spring-like characteristics of the compression portion 720 in combination with the actuation force generated by the linkage assembly 650 provide the handle assembly 500 with a clamping action similar to that of a vice-grip tool to thereby provide a secure and rigid connection between the handle assembly 500 and the broach 60. As should also be appreciated, the secure and rigid connection between the broach 60 and the handle assembly 500 eliminates or at least minimizes motion (e.g., micro-motion) and/or deflection therebetween, thereby providing various advantages including, for example, increased control of the broach 60, increased visual and tactile feedback to the surgeon as to the fit of the broach 60 within the femoral canal, an increased ability of the surgeon to more precisely estimate the resulting tightness of fit of a femoral stem within the femoral canal, and/or easier removal of the broach 60 from the femoral canal subsequent to shaping.

Figure 33:
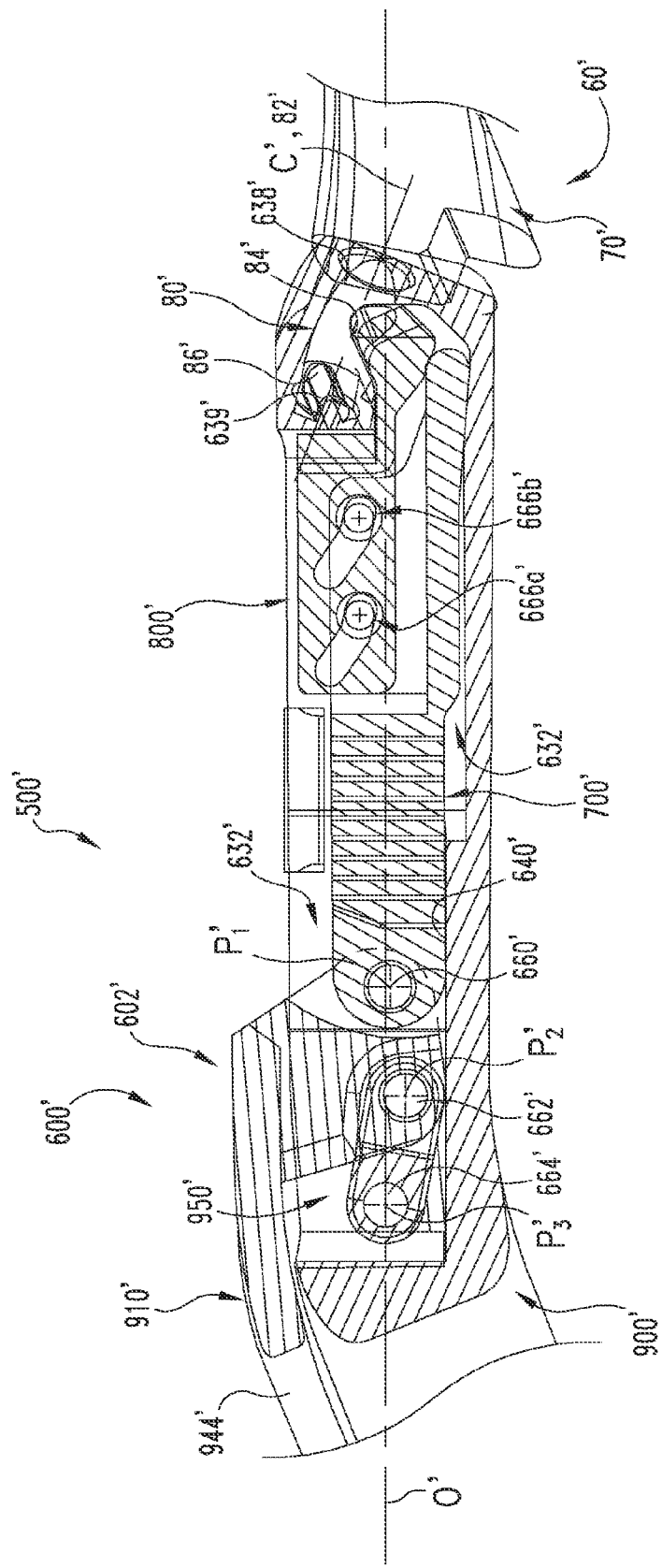
FIG. 33 is a partial cross-section of the portion of the surgical instrument handle assembly shown in FIG. 31A.

Referring to FIGS. 31-33, shown therein is a surgical instrument handle assembly 500' according to another form of the invention configured for preparation of the intramedullary canal of a femur in a total hip replacement surgery or other orthopedic surgeries. The handle assembly 500' has many of the same components and features as the handle assembly 500 illustrated and described above, with like components being referred to using like reference numbers.

The handle assembly 500' is likewise configured for rigid and releasable connection to an orthopedic shaping/cutting device such as, for example, a broach 60'. The broach 60' is configured similar to the broach 60 illustrated and described above. Similar to the broach 60, the broach 60' includes a shaping body portion 70' and a connection post or stem portion 80' extending therefrom and arranged generally along a post axis 82' that is co-axial with the connection axis C' of the distal post-receiving passage 638' defined by the handle assembly 500', and with the connection post 80' likewise defining a transverse notch or groove 84' and an axial notch or groove 86' (FIG. 33). In one embodiment, the shaping body 70' extends along a longitudinal axis 72' and has a shape that generally matches that of a femoral implant to be subsequently inserted into the femoral medullary canal subsequent to preparation of the canal, and also includes a plurality of cutting teeth or other cutting/shaping features configured to remove material from the femoral intramedullary canal to shape the canal. The post axis 82' of the connection post 80' may be arranged either parallel with or oblique to the longitudinal axis 72' of the shaping body 70'. Although a particular type and configuration of the broach 60' has been illustrated and described herein, it should be understood that other types and configurations are also contemplated as would occur to one having ordinary skill in the art. In addition to the broach 60', the handle assembly 500' may also be used in association with other configurations of broaches, other types and configurations of shaping/cutting members, other orthopedic devices, or orthopedic implants.

Similar to the handle assembly 500, the handle assembly 500' is likewise provided with a handle 600' including an elongate shaft 602' having an axial shaft portion 603a', an offset shaft portion 603b', and a distal transition portion 603c'. Additionally, the handle assembly 500' is similarly provided with a linkage assembly 650' (FIG. 33) movably connected to the handle 600' and generally including a compression element 700', a clamp element 800', and an actuator mechanism 900', with the actuator mechanism 900' configured as a toggle-type actuator including a toggle handle 910' and a toggle link 950'. As should be appreciated, the linkage assembly 650' of the handle assembly 500' is structurally and functionally similar to the linkage assembly 650 illustrated and described above with regard to the handle assembly 500. The handle assembly 500' likewise operates in a manner similar to that of the handle assembly 500 to provide a secure and rigid connection of the handle assembly 500' with the shaping member 60'. However, structural differences between certain components of the handle assembly 500' and corresponding components of the handle assembly 500 may be apparent. Some of these structural differences are illustrated in FIGS. 31-33 in association with the following description.

As indicated above, the illustrated embodiment of the handle 600' includes an axial shaft portion 603a', an offset shaft portion 603b', and a distal transition portion 603c'. The axial shaft portion 603a' has a linear configuration arranged generally along a longitudinal axis L'. The axial shaft portion 603a' further defines a recess or indentation 626' sized and shaped to provide access to the lever portion 944' of the toggle handle 910' such that the lever portion 944' may be readily grasped and manipulated by one or more fingers and/or the thumb of the surgeon. In the illustrated embodiment, the recess or indentation 626' extends partially into the axial shaft portion 603a' a distance sufficient to provide access to the lever portion 944'. However, in other embodiments, the recess 626' may extend entirely through the thickness of the axial shaft portion 603a'. The offset shaft portion 603b' extends from the axial shaft portion 603a' and is arranged generally along an offset axis O' that defines one or more angular offsets relative to the longitudinal axis L'. In the illustrated embodiment, the offset axis O' of the offset shaft portion 603b' defines both an anterior offset and a lateral offset relative to the longitudinal axis L'. However, other embodiments are also contemplated where the offset shaft portion 603b' is arranged such that the offset axis O' defines a single offset or other types of compound offsets relative to the longitudinal axis L'. As should be appreciated, providing the elongate shaft 602' with one or more angular offsets (via inclusion of the offset shaft portion 603b') may be beneficial when inserting the shaping member 60' into the femoral intramedullary canal using an anterior surgical approach to minimize interference with adjacent soft tissues or other anatomic structures surrounding the hip joint of the patient.

The distal transition portion 603c' extends from the offset shaft portion 603b' and defines a distal post-receiving passage 638' (similar to the distal post-receiving passage 638 defined by the handle assembly 500) sized and shaped for receipt of the connection post 80' of the broach 60'. The distal post-receiving passage 638' is arranged along a connection axis C' which may be oriented either parallel to or arranged at an oblique angle relative to the offset axis O'. However, other embodiments are also contemplated wherein the elongate shaft 602' does not include a distal transition portion 603c', with the distal post-receiving passage 638' defined by a distal region of the offset shaft portion 603b'. In the illustrated embodiment, the connection axis C' is arranged oblique to the longitudinal axis L' of the axial shaft portion 603a'. However, other embodiments are also contemplated where the connection axis C' may be generally parallel with the longitudinal axis L' of the axial shaft portion 603a'. Additionally, as shown in FIG. 33, the handle shaft 602' defines a projection 639' extending into the post-receiving passage 638' and arranged generally along the connection axis C'. The projection 639' is sized and shaped for receipt within the axial notch or groove 86' formed in the end of the connection post 80' of the broach 60'. Receipt of the projection 639' within the axial notch 86' in the broach connection post 80' provides an added degree of strength and rigidity to the interconnection of the broach 60' with the handle assembly 500'.

In the illustrated embodiment, the handle 600' includes a strike plate or impaction platform 604' similar in structure and function to the impaction platform 604 illustrated and described above. The impaction platform 604' is operatively attached to a proximal end portion of the axial shaft portion 603a' and has a normal proximally-facing impact or strike surface 606', and further includes an angled proximally-facing impact or strike surface 608' arranged at an oblique angle relative to the strike surface 606'. It should be understood that the impaction platform 604' may be provided with additional obliquely-oriented proximally-facing impact or strike surfaces. As should be appreciated, inclusion of the obliquely-oriented proximally-facing impact or strike surfaces 608' allows the surgeon to apply impact forces along axes that are not parallel with the longitudinal axis L'. Other shapes and configurations of the impaction platform 604' and the strike surfaces 606', 608' are also contemplated including, for example, non-rectangular shapes and configurations of the impaction platform 604' and/or impact or strike surfaces 606', 608' having a curved or curvi-linear configuration.

In the illustrated embodiment, the axial shaft portion 603a', the offset shaft portion 603b', and the distal transition portion 603c' each have a generally linear configuration and each define a generally rectangular outer transverse cross-section. However, other shapes and configurations are also contemplated. At least the offset shaft portion 603b' and the distal transition portion 603c' define a hollow interior or inner chamber 632' to house the components of the linkage assembly 650'. The offset shaft portion 603b' may be provided with a number of slotted openings 634' extending transversely through one or more shaft walls and into communication with the hollow interior 632'. The offset shaft portion 603b' and/or the distal transition portion 603c' may also define a window 636' extending transversely therethrough and into communication with the hollow interior 632' adjacent the interconnection of the connection post 80' of the broach 60' with the projection 639' defined by the handle shaft 602'. The openings 634' and the window 636' provide ready access to the components contained within the hollow interior 632', aid in manufacturing, assembly and/or maintenance of the handle assembly 500', facilitate cleaning and/or sterilization of the handle assembly 500', and/or may provide direct visualization of the components contained within the hollow interior 632' to verify proper operation.

In the illustrated embodiment, the offset shaft portion 603b' is also provided with a number of raised lands or plateaus 640' extending inwardly into the hollow interior 632' and defining generally flat/planar bearing surfaces configured to guide the compression element 700' and/or the clamp element 800' in a direction generally parallel with the offset axis O' upon actuation of the actuator mechanism 900'. It should be understood that other features or structures may also be provided to further aid in guiding the compression element 700' and/or the clamp element 800' in a direction generally along the offset axis O' and/or to add strength and structural integrity to the linkage assembly 650'. For example, one or more guide pins may be positioned at locations along the hollowing interior 632' to further aid in guiding the compression element 700' and/or the clamp element 800' upon actuation of the actuator mechanism 900'. Additionally, an end portion or head of the pivot pin 660' (FIG. 31A) that pivotally connects the compression element 700' with the toggle handle 910' may be slidably displaced along an axial slot or groove 637' formed in a side wall of the offset shaft portion 603b' to add further strength and structural integrity to the linkage assembly 650'. A portion of the compression element 700' may also be slidably displaced along an axial slot or groove formed in a side wall of the offset shaft portion 603b' to add further strength and structural integrity to the linkage assembly 650'.

Referring specifically to FIG. 33, the linkage assembly 650' generally includes a compression element 700', a clamp element 800', and an actuator mechanism 900' comprised of a toggle handle 910' and a toggle link 950'. In the illustrated embodiment, the components of the linkage assembly 650' are interconnected via a series of pins or shafts. Specifically, a proximal portion of the compression element 700' is pivotally connected to a first portion of the toggle handle 910' via a first pivot pin 660' extending along a first pivot axis $P_1'$ to permit pivotal movement of the toggle handle 910' relative to the compression element 700' about the first pivot axis $P_1'$. A second portion of the toggle handle 910' is pivotally connected to a distal portion of the toggle link 950' via a second pivot pin 662' extending along a second pivot axis $P_2'$ to permit pivotal movement of the toggle handle 910' relative to the toggle link 950' about the second pivot axis $P_2'$. Additionally, a proximal portion of the toggle link 950' is pivotally connected to the offset shaft portion 603b' of the shaft 602' via a third pivot pin 664' extending along a third pivot axis $P_3'$ to permit pivotal movement of the toggle link 950' relative to the handle 600' about the third pivot axis $P_3'$ while preventing axially displacement of the toggle link 950' along the offset axis O'. Furthermore, a distal portion of the compression element 700' is slidably attached to the clamp element 800' via a pair of dowel pins 666a', 666b'. As should be appreciated, the linkage assembly 650' operates in a manner similar to the linkage assembly 650 illustrated and described above, and therefore need not be discussed in further detail.

While the instruments and devices described herein have been described for use in association with femoral intramedullary canal preparation, it should be understood that the instruments and devices may also be used in association with other surgical procedures and/or in the preparation of other bones or bony structures. In reading the claims, words such as "a", "an", "at least one", and "at least a portion" are not intended to limit the claims to only one item unless specifically stated to the contrary. Additionally, when the language "at least a portion" and/or "a portion" is used, the claims may include a portion and/or the entire item unless specifically stated to the contrary. Furthermore, when the term "distal" is used with respect to a structure, the term refers to the far end of the structure, and when the term "proximal" is used with respect to a structure, the term refers to the near end of the structure.

Various changes and modifications to the described embodiments described herein will be apparent to those skilled in the art, and such changes and modifications can be made without departing from the spirit and scope of the invention and without diminishing its intended advantages. Additionally, while the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

What is claimed is:

1. A surgical instrument handle assembly for releasable connection to an orthopedic device, comprising:
    an elongate shaft including a shaft portion extending generally along a shaft axis and defining an inner chamber at least partially bound by a shaft wall;
    a clamp element at least partially positioned within said inner chamber, said clamp element including a distal end portion having a bearing portion and a head portion;
    a compression element at least partially positioned within said inner chamber and including a flexibly elastic portion and a distal engagement portion, said distal engagement portion positioned between said shaft wall and said distal end portion of said clamp element; and
    an actuator including an initial state and an actuated state, said actuator operatively coupled to said flexibly elastic portion of said compression element, said actuator structured to displace said compression element generally along said inner chamber and to slidably engage said distal engagement portion of said compression element against said bearing portion of said clamp element when transitioned from said initial state toward said actuated state; and
    an orthopedic device including a body portion and a connection portion extending from said body portion, said connection portion arranged along a connection axis, said connection portion positioned in said inner chamber of said shaft portion and compressingly engaged by said head portion of said clamp element when said actuator is transitioned to said actuated state to thereby rigidly and releasably connect said orthopedic device to said elongate shaft.

2. The handle assembly of claim 1, wherein said connection axis is arranged at an oblique angle relative to said shaft axis.

3. The handle assembly of claim 1, wherein said clamp element and said compression element are substantially entirely contained within said inner chamber of said shaft portion.

4. The handle assembly of claim 1, wherein said body portion of said orthopedic device extends along a longitudinal axis, said longitudinal axis arranged at an oblique angle relative to said connection axis.

5. The handle assembly of claim 4, wherein said longitudinal axis of said body portion is arranged generally parallel with and offset from said shaft axis when said orthopedic device is releasably connected to said elongate shaft.

6. The handle assembly of claim 1, wherein said body portion of said orthopedic device includes one or more cutting elements configured to shape or cut bone.

7. The handle assembly of claim 6, wherein said orthopedic device comprises a broach and wherein said one or more cutting elements include a plurality of cutting teeth positioned along said body portion.

8. The handle assembly of claim 1, wherein said connection portion comprises a post, said post defining a transverse notch extending into a side surface of said post; and
wherein said head portion of said clamp element is received in said transverse notch when said actuator is in said actuated position.

9. The handle assembly of claim 8, wherein said head portion of said clamp element
defines a V-shaped projection and wherein said transverse notch has a V-shaped configuration, said V-shaped projection sized and shaped for receipt within said V-shaped notch.

10. The handle assembly of claim 1, further comprising a proximal end portion including a strike plate defining a generally planar impaction surface.

11. The handle assembly of claim 1, wherein said shaft portion has a generally linear configuration and defines a generally rectangular outer transverse cross-section.

12. The handle assembly of claim 1, wherein said actuator comprises a toggle assembly including link pivotally attached to said elongate shaft and a lever pivotally connected to said link and to a proximal portion of said compression element; and
wherein pivotal movement of said lever correspondingly displaces said compression element generally along said inner chamber.

13. The handle assembly of claim 1, wherein said compression element is slidably attached to said clamp element by one or more pins slidably received in a corresponding number of slots.

14. The handle assembly of claim 13, wherein said slots extend at an oblique angle relative to said shaft axis to permit a degree of relative axial movement of said clamp element relative to said compression element generally along a first vector arranged generally parallel with said shaft axis and a degree of relative transverse movement of said clamp element relative to said compression element generally along a second vector arranged transverse to said shaft axis.

15. The handle assembly of claim 1, wherein said flexibly elastic portion of said compression element comprises a spring-like member having spring-like characteristics exhibiting flexibly elastic resiliency generally along a longitudinal axis of said compression element.

16. The handle assembly of claim 1, wherein said flexibly elastic portion of said compression element includes a first series of slits extending from a first side and transversely across a portion of an overall width dimension and a second series of slits extending from a second side opposite said first side and transversely across a portion of said overall width dimension, said first series of slits offset from and interposed between said second series of slits.

17. The handle assembly of claim 1, wherein said flexibly elastic portion of said compression element includes a relatively narrow strip of material extending along a longitudinal axis of said compression element in an undulating or sinusoidal configuration.

18. The handle assembly of claim 1, wherein said bearing portion of said clamp element and said distal engagement portion of said compression element together define a wedge configuration wherein relative axial displacement between said clamp element and said compression element results in transverse displacement of said clamp element and compressed engagement of said head portion of said clamp element against said connection portion of said orthopedic device.

19. The handle assembly of claim 18, wherein said bearing portion of said clamp element defines at least one ramped surface slidably engaged by a distal end portion of said compression element to provide said wedge configuration.

20. The handle assembly of claim 1, wherein said bearing portion of said clamp element defines at least one ramped surface slidably engaged by a distal end portion of said compression element.

21. The handle assembly of claim 20, wherein sliding engagement of said distal end portion of said compression element with said ramped surface of said clamp element transversely displaces said head portion of said clamp element against said connection portion of said orthopedic device to thereby rigidly and releasably connect said orthopedic device to said elongate shaft.

22. The handle assembly of claim 1, wherein said distal engagement portion of said compression element is slidably engaged between said shaft wall and said bearing portion of said clamp element when said actuator is transitioned toward said actuated state to transversely displace said head portion of said clamp element against said connection portion of said orthopedic device to thereby rigidly and releasably connect said orthopedic device to said elongate shaft.

23. A surgical instrument handle assembly for releasable connection to an orthopedic device, comprising:
an elongate shaft including an axial shaft portion arranged generally along a longitudinal axis and an offset shaft portion extending from the axial shaft portion and arranged generally along an offset axis, said offset axis defining at least one angular offset relative to said longitudinal axis, said offset shaft portion defining an inner chamber at least partially bound by a shaft wall;
a clamp element at least partially positioned within said inner chamber, said clamp element including a distal end portion having a bearing portion and a head portion;
a compression element at least partially positioned within said inner chamber and including a flexibly elastic portion and a distal engagement portion, said distal engagement portion positioned between said shaft wall and said distal end portion of said clamp element; and
an actuator including an initial state and an actuated state, said actuator operatively coupled to said flexibly elastic portion of said compression element, said actuator structured to displace said compression element generally along said inner chamber and to slidably engage said distal engagement portion of said compression element against said bearing portion of said clamp element when transitioned from said initial state toward said actuated state; and
an orthopedic device including a body portion and a connection portion extending from said body portion, said connection portion arranged along a connection axis, said connection portion positioned in said inner chamber of said offset shaft portion and compressingly engaged by said head portion of said clamp element when said actuator is transitioned to said actuated state to thereby rigidly and releasably connect said orthopedic device to said elongate shaft.

24. The handle assembly of claim 23, wherein said offset axis is angularly offset relative to said longitudinal axis in at least two different directions to thereby define a compound angular offset between said offset shaft portion and said axial shaft portion.

25. The handle assembly of claim 24, wherein said offset axis is angularly offset relative to said longitudinal axis in both an anterior direction and a lateral direction.

26. The handle assembly of claim 23, wherein said offset shaft portion includes a distal transition portion, said distal transition portion defining a passage in communication with said inner chamber, said passage sized and shaped for receipt of the connection portion of the orthopedic device therein such that said passage is arranged generally along said connection axis when said connection portion is received in said passage; and wherein said connection axis is arranged at an oblique angle relative to said offset axis.

27. The handle assembly of claim 26, wherein said connection axis is arranged at an oblique angle relative to said longitudinal axis of said axial shaft portion.

28. The handle assembly of claim 26, wherein said connection axis is arranged generally parallel with said longitudinal axis of said axial shaft portion.

29. The handle assembly of claim 23, wherein said clamp element and said compression element are substantially entirely contained within said inner chamber of said offset shaft portion.

30. The handle assembly of claim 23, further comprising a proximal end portion including a strike plate defining a generally planar impaction surface.

31. The handle assembly of claim 23, wherein said actuator comprises a toggle assembly including link pivotally attached to said elongate shaft and a lever pivotally connected to said link and a proximal portion of said compression element; and wherein pivotal movement of said lever correspondingly displaces said compression element generally along said inner chamber.

32. The handle assembly of claim 23, wherein said flexibly elastic portion of said compression element comprises a spring-like member having spring-like characteristics exhibiting flexibly elastic resiliency generally along a longitudinal axis of said compression element.

33. The handle assembly of claim 23, wherein said bearing portion of said clamp element and said distal engagement portion of said compression element together define a wedge configuration wherein relative axial displacement between said clamp element and said compression element results in transverse displacement of said clamp element and compressed engagement of said head portion of said clamp element against said connection portion of said orthopedic device.

34. The handle assembly of claim 23, wherein said bearing portion of said clamp element defines at least one ramped surface slidably engaged by a distal end portion of said compression element.

35. The handle assembly of claim 34, wherein sliding engagement of said distal end portion of said compression element with said ramped surface of said clamp element transversely displaces said head portion of said clamp element against said connection portion of said orthopedic device to thereby rigidly and releasably connect said orthopedic device to said elongate shaft.

36. The handle assembly of claim 23, wherein said distal engagement portion of said compression element is slidably engaged between said shaft wall and said bearing portion of said clamp element when said actuator is transitioned toward said actuated state to transversely displace said head portion of said clamp element against said connection portion of said orthopedic device to thereby rigidly and releasably connect said orthopedic device to said elongate shaft.

* * * * *